US011961226B2

United States Patent
Xiao et al.

(10) Patent No.: US 11,961,226 B2
(45) Date of Patent: Apr. 16, 2024

(54) MEDICAL IMAGE RECOGNITION METHOD, MODEL TRAINING METHOD, AND COMPUTER DEVICE

(71) Applicant: Tencent Technology (Shenzhen) Company Limited, Guangdong (CN)

(72) Inventors: Kaiwen Xiao, Shenzhen (CN); Zhongqian Sun, Shenzhen (CN); Chen Cheng, Shenzhen (CN); Wei Yang, Shenzhen (CN)

(73) Assignee: Tencent Technology (Shenzhen) Company Limited, Shenzhen (CN)

( * ) Notice: Subject to any disclaimer, the term of this patent is extended or adjusted under 35 U.S.C. 154(b) by 757 days.

(21) Appl. No.: 17/078,266

(22) Filed: Oct. 23, 2020

(65) Prior Publication Data

US 2021/0042564 A1 Feb. 11, 2021

Related U.S. Application Data

(63) Continuation of application No. PCT/CN2019/114090, filed on Oct. 29, 2019.

(30) Foreign Application Priority Data

Nov. 1, 2018 (CN) .......................... 201811296263.6

(51) Int. Cl.
*G06T 7/00* (2017.01)
*G06F 16/583* (2019.01)
(Continued)

(52) U.S. Cl.
CPC ........ *G06T 7/0012* (2013.01); *G06F 16/5854* (2019.01); *G06F 18/214* (2023.01);
(Continued)

(58) Field of Classification Search
CPC ...... G06T 7/0012; G16H 30/20; G16H 30/40; G16H 50/70; G16H 50/20; G16H 70/20;
(Continued)

(56) References Cited

U.S. PATENT DOCUMENTS

| 2016/0338659 A1 | 11/2016 | Hoshino et al. |
| 2018/0033144 A1* | 2/2018 | Risman ................. G06T 7/0014 |
| 2018/0276813 A1* | 9/2018 | Gur ........................ G06T 7/0012 |

FOREIGN PATENT DOCUMENTS

| CN | 106780460 | 5/2017 |
| CN | 107563983 | 1/2018 |

(Continued)

OTHER PUBLICATIONS

International Search Report dated Jan. 23, 2020 in PCT Application No. PCT/2019/114090 (with English Translation).
(Continued)

*Primary Examiner* — Khai M Nguyen
(74) *Attorney, Agent, or Firm* — ARENTFOX SCHIFF LLP

(57) ABSTRACT

In a medical image recognition method, applied to a computer device, a to-be-recognized medical image set is obtained, where the to-be-recognized medical image set includes at least one to-be-recognized medical image. A to-be-recognized area corresponding to each to-be-recognized medical image in the to-be-recognized medical image set is extracted. The to-be-recognized area is a part of the to-be-recognized medical image. A recognition result of each to-be-recognized area through a medical image recognition model is determined. The medical image recognition model is obtained through training according to a medical image sample set. The medical image sample set includes at least one medical image sample, and each medical image sample carries corresponding annotation information. The annotation information is used for representing a type of the
(Continued)

medical image sample, and the recognition result is used for representing the a of the to-be-recognized medical image.

16 Claims, 9 Drawing Sheets

(51) Int. Cl.
| | |
|---|---|
| G06F 18/214 | (2023.01) |
| G06V 10/32 | (2022.01) |
| G06V 10/75 | (2022.01) |
| G06V 10/774 | (2022.01) |
| G16H 30/20 | (2018.01) |
| G16H 30/40 | (2018.01) |
| G16H 50/20 | (2018.01) |
| G16H 50/70 | (2018.01) |
| G16H 70/20 | (2018.01) |
| A61B 5/055 | (2006.01) |
| A61B 6/00 | (2006.01) |
| A61B 8/08 | (2006.01) |
| G06F 17/11 | (2006.01) |

(52) U.S. Cl.
CPC ............ *G06V 10/32* (2022.01); *G06V 10/751* (2022.01); *G06V 10/774* (2022.01); *G16H 30/20* (2018.01); *G16H 30/40* (2018.01); *G16H 50/20* (2018.01); *G16H 50/70* (2018.01); *G16H 70/20* (2018.01); *A61B 5/055* (2013.01); *A61B 6/5217* (2013.01); *A61B 8/5223* (2013.01); *G06F 17/11* (2013.01); *G06V 2201/03* (2022.01)

(58) Field of Classification Search
CPC .... G06F 16/5854; G06F 18/214; G06F 17/11; G06V 10/32; G06V 10/751; G06V 10/774; G06V 2201/03; A61B 5/055; A61B 6/5217; A61B 8/5223
See application file for complete search history.

(56) References Cited

FOREIGN PATENT DOCUMENTS

| | | | | |
|---|---|---|---|---|
| CN | 109461495 | | 3/2019 | |
| CN | 112384892 A | * | 2/2021 | ........... G06K 9/6229 |
| EP | 0851664 A2 | * | 11/1997 | |
| EP | 851664 A2 | * | 7/1998 | ........... H04N 1/4074 |
| EP | 3188081 B1 | * | 5/2021 | ......... G06K 9/00624 |
| JP | 2015106307 A | | 6/2015 | |
| JP | 2017227993 A | | 12/2017 | |
| JP | 2018-117883 A | | 8/2018 | |
| JP | 6801490 B2 | * | 12/2020 | ......... G06K 9/00624 |
| JP | 2022113972 A | * | 8/2022 | |
| WO | 2015015851 A1 | | 2/2015 | |
| WO | 2018098077 A1 | | 5/2018 | |

OTHER PUBLICATIONS

Written Opinion dated Jan. 23, 2020 in PCT Application No. PCT/2019/114090.
Japanese Office Action dated Jan. 11, 2022 in Application No. 2021-508060 with English Translation.
Kaori Nomura, "Reconstruction of 3D Ultrasound Images and Robust Artery Region Extraction for a Computer Aided FMD Test System with a H-type Probe", Computer Vision and Image Media (CVIM) 2016-CVIM-201 [online], Information Processing Society of Japan, Feb. 25, 2016, pp. 1-8.
Extended European Search Report dated Jul. 15, 2021 in European Application No. 19878946.3.
Communication Pursuant to Rules 70(2) and 70a(2) EPC dated Aug. 3, 2021 in European Application No. 19878946.3.
Ghongade et al., "Computer-aided Diagnosis System for Breast Cancer Using RF Classifier", 2017 International Conference on Wireless Communications, Signal Processing and Networking (WISPNET), IEEE, Mar. 22, 2017, XP033324183, pp. 1068-1072.
Japanese Office Action dated Aug. 29, 2022 in Application No. 2021-508060 with English Translation (9 pages).

* cited by examiner

MEDICAL IMAGE RECOGNITION METHOD, MODEL TRAINING METHOD, AND COMPUTER DEVICE

RELATED APPLICATION

This application is a continuation of International Application No. PCT/CN2019/114090, filed on Oct. 29, 2019, which claims priority to Chinese Patent Application No. 201811296263.6, entitled "MEDICAL IMAGE RECOGNITION METHOD, MODEL TRAINING METHOD, AND SERVER" and filed on Nov. 1, 2018. The entire disclosures of the prior applications are hereby incorporated by reference in their entirety.

FIELD OF THE TECHNOLOGY

The present disclosure relates to the field of artificial intelligence (AI) including a medical image recognition method, a model training method, and a computer device.

BACKGROUND OF THE DISCLOSURE

With the generation and rapid development of medical imaging technologies such as computed tomography (CT), magnetic resonance imaging (MRI), and ultrasonic (US), hospitals generate and store a large quantity of medical images available for clinical diagnosis and analysis. In recent years, computer and related technologies develop rapidly and the graphics and image technology mature day by day, a medical worker may observe a medical image from a plurality of directions, levels, and angles, so as to assist a doctor in emphatically analyzing pathological body and other areas of interest, thereby improving the accuracy of clinical diagnosis.

Currently, the recognition of medical images mainly involves medical workers first annotating medical images to obtain (or indicate) anomalies and report the anomalies to medical institutions or medical experts for confirmation. Some major imaging centers also categorize and store confirmed medical images for analysis and study.

However, it takes medical workers a lot of time to annotate a large quantity of medical images, resulting in relatively high annotation costs. In addition, manual annotation of medical images is prone to errors, leading to lower reliability and accuracy of medical image recognition.

SUMMARY

According to exemplary aspects, in a medical image recognition method, applied to a computer device, a to-be-recognized medical image set is obtained, where the to-be-recognized medical image set includes at least one to-be-recognized medical image. A to-be-recognized area corresponding to each to-be-recognized medical image in the to-be-recognized medical image set is extracted. The to-be-recognized area is a part of the to-be-recognized medical image. A recognition result of each to-be-recognized area through a medical image recognition model is determined. The medical image recognition model is obtained through training according to a medical image sample set. The medical image sample set includes at least one medical image sample, and each medical image sample carries corresponding annotation information. The annotation information is used for representing a type of the medical image sample, and the recognition result is used for representing a type of the to-be-recognized medical image.

According to exemplary aspects, in a model training method, applied to a computer device, a to-be-trained medical image sample set is obtained. The medical image sample set includes at least one medical image sample. Each medical image sample carries corresponding annotation information, where the annotation information is used for representing a type of the medical image sample. A to-be-trained area corresponding to each medical image sample in the medical image sample set is extracted. The to-be-trained area is a part of the medical image sample. A medical image recognition model is obtained through training according to the to-be-trained area corresponding to each medical image sample and the corresponding annotation information carried by each medical image sample.

According to exemplary aspects, a computer device includes a memory and a processor that obtains a to-be-recognized medical image set. The to-be-recognized medical image set includes at least one to-be-recognized medical image. The processor extracts a to-be-recognized area corresponding to each to-be-recognized medical image in the to-be-recognized medical image set. The to-be-recognized area is a part of the to-be-recognized medical image. The processor determines a recognition result of each to-be-recognized area through a medical image recognition model. The medical image recognition model is obtained through training according to a medical image sample set. The medical image sample set includes at least one medical image sample, where each medical image sample carries corresponding annotation information. The annotation information is used for representing a type of the medical image sample, and the recognition result is used for representing a type of the to-be-recognized medical image.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Exemplary embodiments of the present disclosure provide a medical image recognition method, a model training method, and a computer device, so that the manual annotation costs and time costs can be greatly reduced. In addition, the use of the model to recognize a medical image is applicable to a plurality of scenarios, the accuracy of recognition does not vary for different users, and high reliability and credibility are achieved.

The terms "first", "second", "third", "fourth", and the like (if exist) in the specification and the claims of this application and the foregoing accompanying drawings are used for distinguishing similar objects, and do not need to be used for describing a particular sequence or order. It is to be understood that data used in this way is interchangeable in a suitable case, so that the embodiments of this application described herein can be implemented in a sequence in addition to the sequence shown or described herein. Moreover, the terms "include", "have", and any other variations mean to cover the non-exclusive inclusion. For example, a process, method, system, product, or device that includes a list of operations or units is not necessarily limited to those expressly listed steps or units, but may include other steps or units not expressly listed or inherent to such a process, method, system, product, or device.

The exemplary embodiments of the present disclosure may be applied to a medical image processing scenario. With the continuous research and development of medical testing devices and the continuous improvement of testing technologies, medical image data grows exponentially. With the demand for a large amount of medical image data, there are inevitably a lot of irrelevant image data or samples that are contradictory to current research. Such data needs to be effectively eliminated before the entire data set can be used for research, calculation, training, and inference. Therefore, in the actual process, a lot of manpower, material resources, and financial resources are required to perform reselection and elimination on existing data. The data is processed by using the method of precise annotation to meet the accuracy requirement of data.

Figure 1:
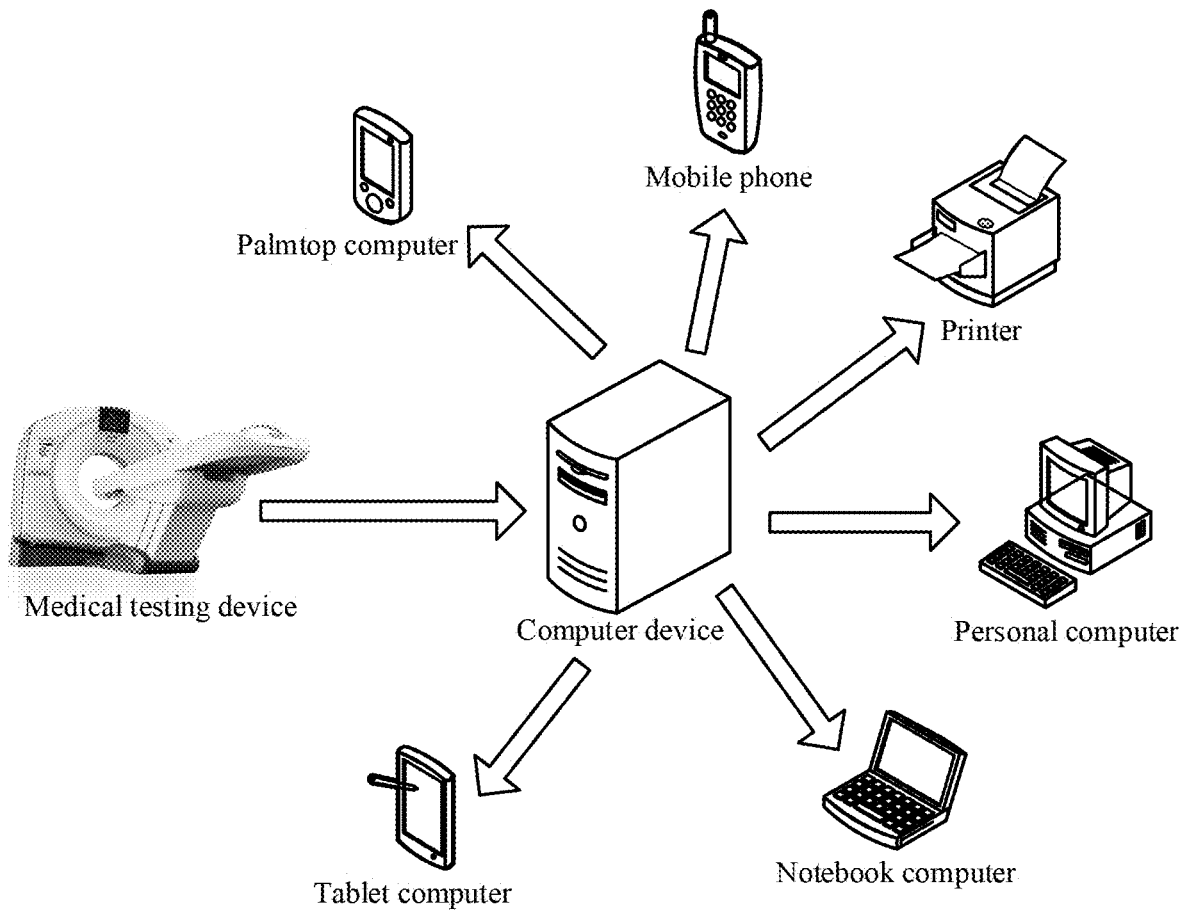
FIG. 1 is a schematic architectural diagram of a medical image recognition system according to an exemplary embodiment of the present disclosure.

Specifically, FIG. 1 is a schematic architectural diagram of a medical image recognition system according to an exemplary embodiment of the present disclosure. As shown in FIG. 1, a large quantity of medical images may be obtained through a medical testing device, and the medical images include, but are not limited to, a CT image, an MRI image, and a US image.

The CT image is formed by a particular quantity of pixels with different grayscales from black to white arranged in a matrix. The pixels reflect the X-ray absorption coefficients of corresponding voxels. The CT images are represented by different grayscales, reflecting the degrees of X-ray absorption of organs and tissues. Therefore, like black and white images shown on X-ray images, black shadows represent areas of low absorption, that is, areas of low density, for example, lungs with a large amount of gas; and white shadows represent areas of high absorption, that is, areas of high density, for example, bones. Through comparison between a CT image and an X-ray image, the CT image has higher density resolution, that is, the CT image has a high density resolution. Therefore, the CT image may better display organs formed by soft tissues, for example, the brain, spinal cord, mediastinum, lung, liver, gallbladder, pancreas, and organs of basin, and may display images of lesions on an adequate anatomical image background.

The MRI image has been applied to imaging diagnosis of all systems of the entire body. The best effects of diagnosis are on the brain, spinal cord, heart and great vessels, joints and bones, soft tissues, pelvic cavity, and the like. For cardiovascular diseases, anatomic changes of chambers, great vessels, and valves can be observed, and ventricular analysis can be performed. Qualitative and semi-quantitative diagnoses are performed, and a plurality of section diagrams may be made, which has relatively high spatial resolution and can display a complete picture of the heart and lesion. In addition, a relationship between the MIRI image and a surrounding structure is preferential to a relationship between the surrounding structure with other X-ray imaging, two-dimensional US, nuclide or CT examination. When the brain spinal cord lesion is diagnosed, coronal images, sagittal images, and section images may be made.

The US image may reflect a difference between acoustic parameters in media, and information different from optics, X-rays, γ-rays, and the like may be obtained. The US has a high capability of distinguishing the soft tissues of human body, which facilitates the identification of small lesions of biological tissues. When the US image displays a viable tissue, a desired image may be obtained without staining.

The medical testing device transmits the medical images to a computer device, and recognizes and classifies the medical images through a model obtained through training in the computer device. A server then transmits an image recognition result to a terminal device. The terminal device may then generate and print a report according to the recognition result or may directly display the recognition result on a display screen. The terminal device includes, but is not limited to, a palmtop computer, a mobile phone, a printer, a personal computer, a notebook computer, and a tablet computer.

The medical testing device, the computer device, and the terminal device included in the medical image recognition system may be three independent devices or may be integrated into one same system, as one of ordinary skill will recognize. It is to be understood that, this application may be specifically applied to data screening of an early lung cancer screening program, and data archiving and confirmation of a medical imaging center on medical image data, or cleaning of historical data.

Figure 2:
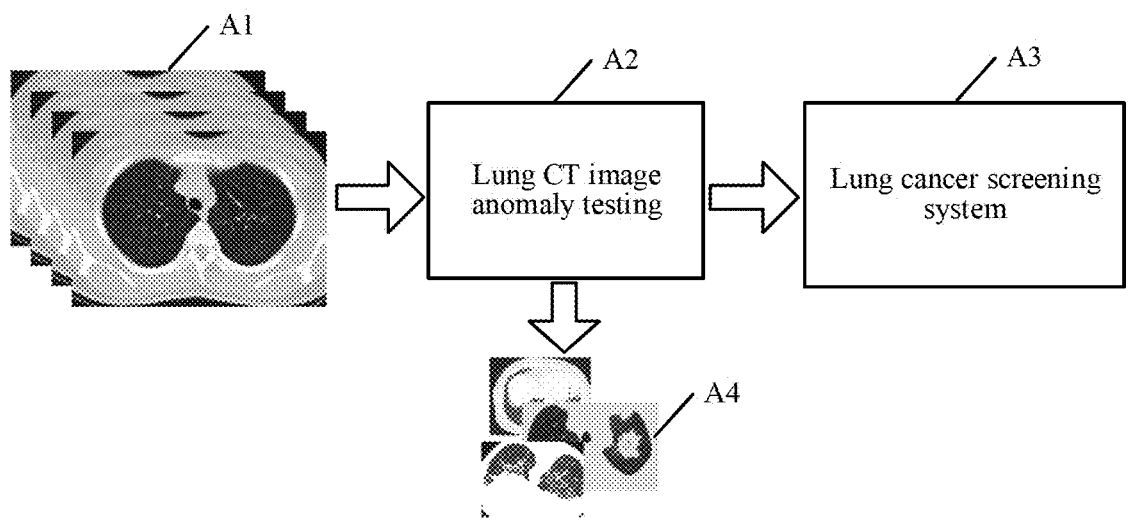
FIG. 2 is a schematic diagram of a scenario in which an exemplary embodiment of the present disclosure is applied to an early lung cancer screening program.

For ease of understanding, FIG. 2 is a schematic diagram of a scenario in which an exemplary embodiment of the present disclosure is applied to an early lung cancer screening program. As shown in FIG. 2, in step A1, a large quantity of original data sets related to lungs are collected through a medical testing device. In step A2, the original data sets are then inputted into a lung CT image anomaly testing system. A medical image recognition model provided in this application is run in the system, and the original data sets are classified by using the medical image recognition model. In step A3, results obtained through classification are inputted into a lung cancer screening system, and the lung cancer screening system counts and screens the classification results, so as to infer the risk of lung cancer. Correspondingly, during testing by using the lung CT image anomaly testing system, images that do not satisfy a classification condition may be screened out, that is, abnormal lung images are screened and excluded in step A4, so as to ensure the reliability of testing.

Figure 3:
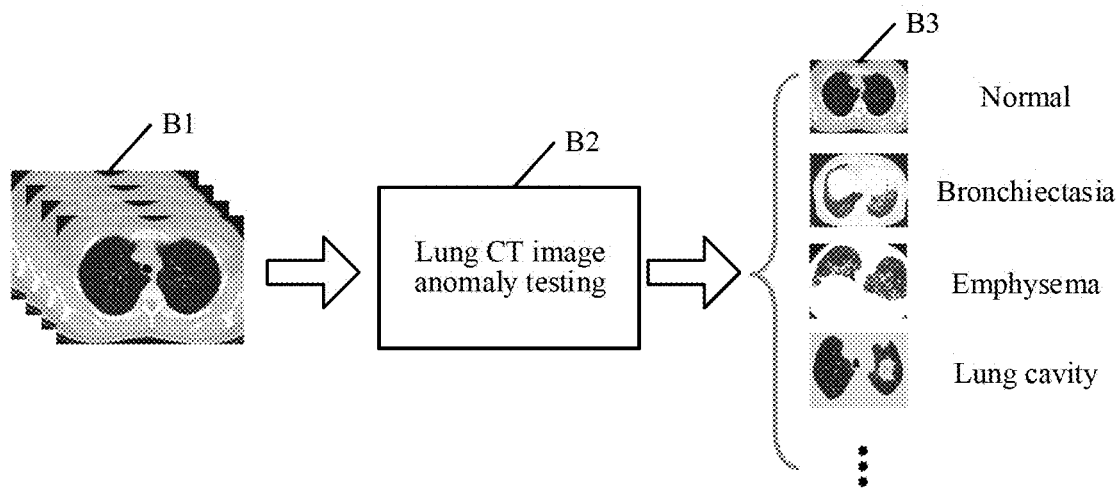
FIG. 3 is a schematic diagram of a scenario in which an exemplary embodiment of the present disclosure is applied to data cleaning of an imaging center.

FIG. 3 is a schematic diagram of a scenario in which an exemplary embodiment of the present disclosure is applied to data cleaning of an imaging center. As shown in FIG. 3, in step B1, a large quantity of original data sets related to lungs is collected through a medical testing device. In step B2, the original data sets are then inputted into a lung CT image anomaly testing system. A medical image recognition model provided in this application is run in the system, and the original data sets are classified by using the medical image recognition model. In step B3, lung CT images are classified according to "normal lung" and "abnormal lung". The CT images of "abnormal lung" are specifically classified according to disease traits and disease types, so as to classify the diseases according to the category of lung CT images, thereby reducing possible noise confusion caused by early lung cancer screening. Various lung images may be classified into symptoms such as bronchiectasia, emphysema, pulmonary atelectasis, exudation, consolidation, proliferation, fibrosis, calcification, lump, node, hole, cavity, pleural effusion, hydropneumothorax, and pneumothorax. Therefore, doctors are assisted or replaced to classify lung images of various diseases, so that the workload is reduced and the efficiency is improved for doctors, and the accuracy of annotation results is improved.

It is to be understood that the present disclosure is described by using a lung image as an example. However, during actual application, the medical image may be alternatively a stomach image, an abdomen image, a brain image or the like. Using the lung image as a medical image is merely an example herein, which is not to be used to limit the present disclosure.

Figure 4:
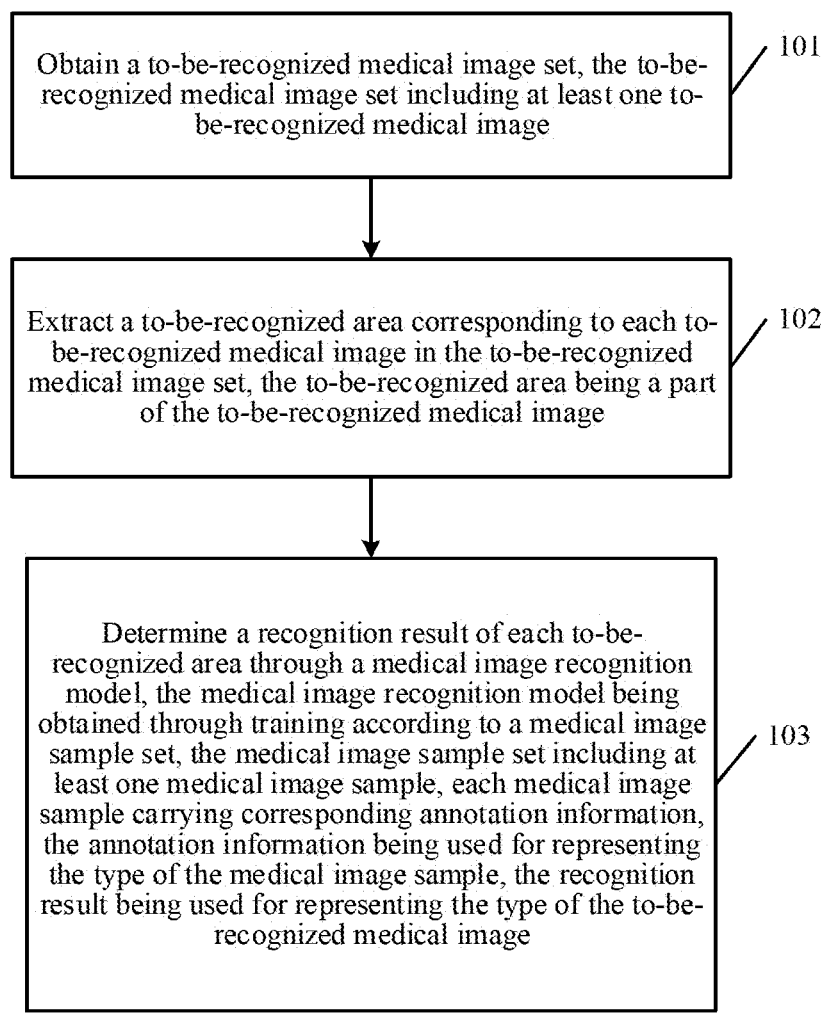
FIG. 4 is a schematic diagram of a medical image recognition method according to an exemplary embodiment of the present disclosure.

The medical image recognition method provided in this application is applied to a computer device, and the computer device may be a server. The following describes the medical image recognition method from the perspective of a server. Referring to FIG. 4, an exemplary embodiment of the medical image recognition method according to the present disclosure includes the following steps.

In step 101, a to-be-recognized medical image set is obtained. The to-be-recognized medical image set includes at least one to-be-recognized medical image.

In an exemplary embodiment, the server obtains the to-be-recognized medical image set. The to-be-recognized medical image set may include only one to-be-recognized medical image or may include a plurality of to-be-recognized medical images. The medical image may be a CT image, an MRI image or a US image. The to-be-recognized medical image may be specifically a lung image, a stomach image, a brain image, a liver image, a heart image or the like. The exemplary embodiments of the present disclosure are described by using the lung image as an example, and it is not to be used to limit the present disclosure.

In step 102, a to-be-recognized area corresponding to each to-be-recognized medical image in the to-be-recognized medical image set is extracted. The to-be-recognized area is a part of the to-be-recognized medical image.

In an exemplary embodiment, after receiving the to-be-recognized medical image set, the server may perform feature extraction on each to-be-recognized medical image to obtain the to-be-recognized area. The to-be-recognized area is a part of the to-be-recognized medical image, and the part can reflect symptom features.

In step 103, a recognition result of each to-be-recognized area is determined through a medical image recognition model. The medical image recognition model is obtained through training according to a medical image sample set. The medical image sample set includes at least one medical image sample, and each medical image sample carries corresponding annotation information. The annotation information is used for representing the type of the medical image sample, and the recognition result is used for representing the type of the to-be-recognized medical image.

In an exemplary embodiment, the server inputs each to-be-recognized area into the medical image recognition model. The medical image recognition model then outputs the recognition result corresponding to each to-be-recognized area. The recognition result may represent the type of the to-be-recognized medical image, for example, "normal", "emphysema", "bronchiectasia" or "calcification". The medical image recognition model is obtained through training by using a large quantity of medical image samples. Each medical image sample carries corresponding annotation information. For example, annotation information of a lung image sample 1 is "normal", annotation information of a lung image sample 2 is "emphysema", annotation information of a lung image sample 3 is "calcification", and the like. The annotation information herein is usually obtained through manual annotation.

Figure 5:
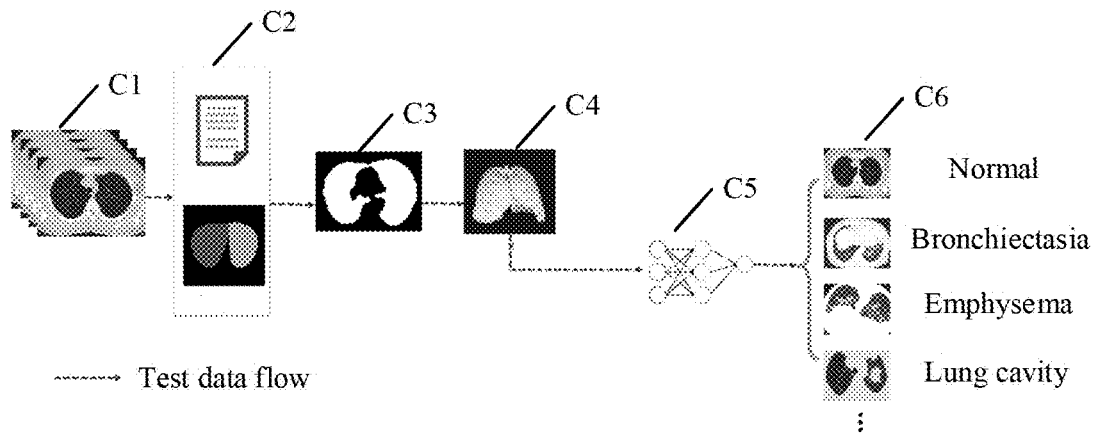
FIG. 5 is a schematic flowchart of recognizing a medical image according to an exemplary embodiment of the present disclosure.

For ease of description, FIG. 5 is a schematic flowchart of recognizing a medical image according to an exemplary embodiment of the present disclosure. Specifically, in step C1, a server acquires a large quantity of original data sets related to lungs through a medical testing device. In step C2, each medical image in the original data set is determined through label information and template matching to obtain a recognizable lung image. In step C3, a lung area in the recognizable lung image is segmented and extracted, and in step C4, image interpolation and normalization are performed on the segmented and extracted lung area. In step C5, the lung area obtained in step C4 is classified and inferred by using a deep learning network, and in step C6, a corresponding recognition result such as "normal", "bronchiectasia", "emphysema" or "lung cavity" is obtained.

In an exemplary embodiment of the present disclosure, a medical image recognition method is provided. First, a server obtains a to-be-recognized medical image set, the to-be-recognized medical image set including at least one to-be-recognized medical image. Then the server extracts a to-be-recognized area corresponding to each to-be-recognized medical image in the to-be-recognized medical image set. The to-be-recognized area is a part of the to-be-recognized medical image. The server then determines a recognition result of each to-be-recognized area through a medical image recognition model. The medical image recognition model is obtained through training according to a medical image sample set, where the medical image sample set includes at least one medical image sample. Each medical image sample carries corresponding annotation information, which is used for representing the type of the medical image sample. The recognition result is used for representing the type of the to-be-recognized medical image. In the foregoing manners, the medical image recognition model is used in place of manual annotation, so that the manual annotation costs and time costs can be greatly reduced. In addition, the use of the model to recognize a medical image is applicable to a plurality of scenarios, the accuracy of recognition does not vary for different users, and relatively high reliability and accuracy are achieved.

Optionally, based on the exemplary embodiment corresponding to FIG. 4, and an exemplary embodiment of the model training method, before obtaining the to-be-recognized medical image set, the method may further include the following steps. In a first step, a to-be-recognized original medical image set is obtained. The to-be-recognized original medical image set includes at least one to-be-recognized original medical image. In a second step, label information of each to-be-recognized original medical image in the to-be-recognized original medical image set is obtained. The label information includes information associated with the to-be-recognized original medical image. In a third step, in a case that the label information of the to-be-recognized original medical image satisfies a sample extraction condition, the to-be-recognized original medical image is determined as the to-be-recognized medical image, until the to-be-recognized medical image set is obtained from the to-be-recognized original medical image set.

In an exemplary embodiment, a preprocessing manner of a medical image is described. For both a medical image recognition scenario and a medical image training scenario, first, a medical image that does not meet the requirements of the recognition scenario or the training scenario needs to be eliminated. Specifically, the server first obtains the to-be-recognized original medical image set, the to-be-recognized original medical image set including at least one to-be-recognized original medical image. Next, it needs to be determined whether each to-be-recognized original medical image satisfies the training scenario or the recognition scenario. Finally, to-be-recognized original medical images that do not satisfy the scenarios are eliminated.

During determination, information comparison may be performed on the to-be-recognized original medical image. That is, it is determined whether label information (also referred to as Meta information) corresponding to each to-be-recognized original medical image satisfies a sample extraction condition. The label information includes, but is not limited to, a patient identifier, a hospital identifier, a testing device identifier, tested part information, and testing doctor information corresponding to the to-be-recognized original medical image. An attribute of the label information defines associated names and value pairs.

Certainly, during actual application, if there is a non-CT image in the to-be-recognized original medical image set, these to-be-recognized original medical images also need to be eliminated. Alternatively, the to-be-recognized original medical images that are damaged due to a storage problem or the like also need to be eliminated.

Optionally, based on the exemplary embodiment corresponding to FIG. 4, in a second exemplary embodiment of the model training method according to the embodiments of this application, before obtaining the to-be-recognized medical image set, the method may further include the following steps. In a first step, a to-be-recognized original medical image set, the to-be-recognized original medical image set including at least one to-be-recognized original medical image is obtained. In a second step, label information of each to-be-recognized original medical image in the to-be-recognized original medical image set is obtained. The label information includes information associated with the to-be-recognized original medical image. In a third step, the to-be-recognized original medical image is matched with a target medical image in a case that the label information of the to-be-recognized original medical image satisfies a sample extraction condition. The target medical image is a preset image template. In a fourth step, in a case that the to-be-recognized original medical image is successfully matched with the target medical image, the to-be-recognized original medical image is determined as the to-be-recognized medical image, until the to-be-recognized medical image set is obtained from the to-be-recognized original medical image set In an exemplary embodiment, another preprocessing manner of a medical image is described. For both a medical image recognition scenario and a medical image training scenario, first, a medical image that does not meet the requirements of the recognition scenario or the training scenario needs to be eliminated. Specifically, the server first obtains the to-be-recognized original medical image set, the to-be-recognized original medical mage set including at least one to-be-recognized original medical image. Next, it needs to be determined whether each to-be-recognized original medical image satisfies the training scenario or the recognition scenario. Finally, to-be-recognized original medical images that do not satisfy the scenarios are eliminated.

Certainly, during actual application, if there is a non-CT image in the to-be-recognized original medical image set, these to-be-recognized original medical images also need to be eliminated. Alternatively, the to-be-recognized original medical images that are damaged due to a storage problem or the like also need to be eliminated. During verification, the lung area and other areas may be distinguished by training a picture classification model, or it is determined in an image pixel statistical distribution manner whether the to-be-recognized original medical image is the lung area.

Optionally, based on the exemplary embodiment corresponding to FIG. 4, in a third exemplary embodiment of the model training method according to the embodiments of this application, the extracting a to-be-recognized area corresponding to each to-be-recognized medical image in the to-be-recognized medical image set may include the following steps. In a first step, binarization on each to-be-recognized medical image in the to-be-recognized medical image set is performed according to a preset reflected value, to obtain a binary medical image corresponding to each to-be-recognized medical image. In a second step, each binary medical image is matched by using a target medical image, to extract a to-be-processed area corresponding to each binary medical image. The target medical image is a preset image template. In a third step, image smoothing is performed on each to-be-processed area, to generate a to-be-extracted outline corresponding to each to-be-processed area. The image smoothing includes performing at least one of an opening operation and a closing operation on each to-be-processed area. In a fourth step, the corresponding to-be-recognized area is extracted from each to-be-recognized medical image by using each to-be-extracted outline.

In an exemplary embodiment, after performing validity verification on the to-be-recognized original medical image, the to-be-recognized medical image may be obtained, where at least one to-be-recognized medical image may form the to-be-recognized medical image sample set. Next, a to-be-recognized area (for example, the lung area) further needs to be extracted from each to-be-recognized medical image. To effectively filter out the noise that may be caused by areas other than the lung field and to make the subsequent model determination more accurate, the calculation amount in addition to the lung field is reduced.

An example of extracting a to-be-recognized area (or a to-be-trained area) from the to-be-recognized medical image is used. First, binarization separation is performed on the medical image sample. That is, the binarization separation is performed on the medical image sample by using an appropriate thresholding method. Different organs and tissues have different reflected values (for example, CT values), and an approximate outline of a lung may be accurately found from the medical image sample according to the CT values. Assuming that a preset reflected value for a lung is 30 hounsfield units (Hu), a binary medical image with Hu of 30 is extracted.

Next, smoothing is performed on a to-be-processed area after a lung lobe area is extracted, to obtain a to-be-extracted outline corresponding to the to-be-processed area. This step specifically includes performing an opening operation or a closing operation on each to-be-processed area, or performing an opening operation and a closing operation at the same time. The opening operation may smooth an outline of an image, open a narrow neck and eliminate a thin protrusion. The performing the opening operation on a set A by using a structural element B is defined as:

$$A \circ B = (A \ominus B) \oplus B \quad A \circ B = (A \ominus B) \oplus B.$$

Meaning: Corrode B with A first, and then expand a result with B.

The closing operation also smooths the outline of the image. However, as opposed to the opening operation, the closing operation can bridge narrow gaps and elongated ravines, eliminate small holes, and fill gaps in the contour line. Performing the closing operation on a set A by using a structural element B is defined as:

$$A \cdot B = (A \oplus B) \ominus B \quad A \cdot B = (A \oplus B) \ominus B.$$

Meaning: Expand B with A first, and then corrode a result with B.

Isolated noise points and holes in the to-be-processed area may be removed by using the opening operation and the closing operation, so that the to-be-processed area is smoother.

Finally, a corresponding to-be-trained area is extracted from each medical image sample by using each to-be-extracted outline. Specifically, after a to-be-extracted outline is obtained, the to-be-extracted outline is used as an index and is returned to the medical image sample to extract the to-be-recognized area (or the to-be-trained area).

Optionally, based on the exemplary embodiment corresponding to FIG. 4, in a fourth exemplary embodiment of the model training method according to the embodiments of this application, after the extracting a to-be-recognized area corresponding to each to-be-recognized medical image in the to-be-recognized medical image set, the method may further include the following steps. In a first step, the to-be-recognized area is scaled down in a case that the to-be-recognized area is larger than or equal to a first preset area. In a second step, the to-be-recognized area is scaled up in a case that the to-be-recognized area is smaller than or equal to a second preset area.

In an exemplary embodiment, after the to-be-recognized area is obtained through segmentation, interpolation further needs to be performed on the to-be-recognized area. An objective is to make a unit physical length in each direction of the image in a three-dimensional image in an equal distance state, which facilitates measurement and model calculation.

In an actual case, different to-be-recognized medical images have different to-be-recognized area sizes. For example, a lung image size of a child is generally less than a lung image size of an adult. In this case, a measuring scale is required. For example, one pixel is equal to 1 mm. If the to-be-recognized area is larger than or equal to the first preset area, it indicates that the size of the to-be-recognized area may be slightly large. In this case, the to-be-recognized area needs to be scaled down according to a ratio, to make the length of each pixel in the to-be-recognized area equal to 1 mm to the greatest extent. In contrast, if the to-be-recognized area is smaller than or equal to a second preset area, it indicates that the size of the to-be-recognized area may be slightly large. In this case, the to-be-processed area needs to be scaled down according to a ratio, to make the length of each pixel in the to-be-recognized area equal to 1 mm to the greatest extent.

Optionally, based on the exemplary embodiment corresponding to FIG. 4, in a fifth exemplary embodiment of the model training method according to the embodiments of this application, after the extracting a to-be-recognized area corresponding to each to-be-recognized medical image in the to-be-recognized medical image set, the method may further include the following steps. In a first step, a reflected value interval corresponding to each to-be-recognized area is obtained. The maximum value of the reflected value interval is a first reflected value, and the minimum value of the reflected value interval being a second reflected value. In a second step, normalization on each to-be-recognized area according to the reflected value interval is performed to obtain a normalized area. In a third step, the determining a recognition result of each to-be-recognized area through a medical image recognition model is performed by determining a recognition result corresponding to the normalized area of each to-be-recognized area through the medical image recognition model. The performing the performing normalization on each to-be-recognized area according to the reflected value interval, to obtain a normalized area includes obtaining the normalized area using the following equation:

$$x_{out} = \frac{x - x_{min}}{x_{max} - x_{min}},$$

Where $x_{out}$ represents the normalized area, x represents a pixel value of the to-be-recognized area, $x_{max}$ represents the first reflected value, and $x_{min}$ represents the second reflected value.

In an exemplary embodiment, after the to-be-recognized area is obtained through segmentation, normalization further needs to be performed on the to-be-trained area. An objective is to make all to-be-recognized areas to be in a dimensionally unified state, to facilitate measurement and model calculation.

Specifically, the normalization may integrate all pixels in the image in an interval with a lung window being from −600 Hu to 1024 Hu, and then linearly scale the entire image between 0.0 and 1.0. The window width of the lung window represents a range of a visual CT value, and different content details may be viewed at different window widths. A normalized area may be obtained in an image manner:

$$x_{out} = \frac{x - x_{min}}{x_{max} - x_{min}},$$

Where $x_{out}$ represents the normalized area, x represents a pixel value of the to-be-recognized area, $x_{max}$ represents the first reflected value, and $x_{min}$ represents the second reflected value.

An example in which the lung window s from −600 Hu to 1024 Hu is used above. $x_{max}$ is 1024 and $x_{min}$ is −600. Assuming that x is 1000, the obtained normalized area of $x_{out}$ is represented as 0.985.

Figure 6:
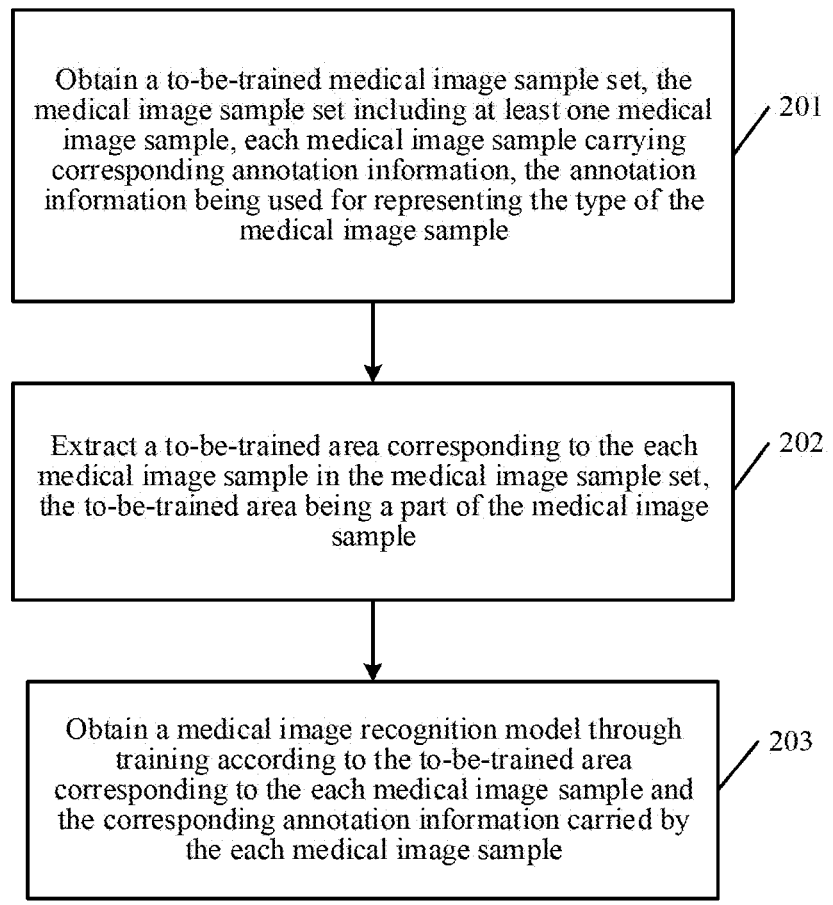
FIG. 6 is a schematic diagram of a model training method according to an exemplary embodiment of the present disclosure.

The model training method provided in this application is applied to a computer device, and the computer device may be a server. The following describes the model training method from the perspective of a server. Referring to FIG. 6, an exemplary embodiment of the model training method according to the present disclosure includes the following steps.

In step 201, a to-be-trained medical image sample set is obtained, the medical image sample set including at least one medical image sample, each medical image sample carrying corresponding annotation information. The annotation information is used for representing the type of the medical image sample.

In an exemplary embodiment, the server first obtains the to-be-trained medical image sample set. The to-be-trained medical image sample set may include only one to-be-trained medical image sample or may include a plurality of to-be-trained medical image samples. The to-be-trained medical image sample may be a CT image sample, an MRI image sample, or a US image sample. The medical image sample may be specifically a lung image, a stomach image, a brain image, a liver image, a heart image or the like. The exemplary embodiments of the present disclosure are described by using the lung image as an example, and it is to not be used to limit the present disclosure.

In step 202, a to-be-trained area corresponding to each medical image sample in the medical image sample set is extracted. The to-be-trained area is a part of the medical image sample.

In an exemplary embodiment, after obtaining the to-be-trained medical image sample set, the server needs to perform feature extraction on each medical image sample to obtain the to-be-trained area. The to-be-trained area is a part of the medical image sample, and the part can reflect symptom features.

In step 203, a medical image recognition model is obtained through training according to the to-be-trained area corresponding to each medical image sample and the corresponding annotation information carried by each medical image sample.

In an exemplary embodiment, the server establishes a deep learning network, and trains and stores the medical image recognition model by using the corresponding annotation information carried by each medical image sample and the to-be-trained area corresponding to each medical image sample. The deep learning network includes, but is not limited to, at least one of neural networks such as a convolutional neural network (CNN), a deep convolutional neural network (DCNN), a deconvolutional network (DN), a generative adversarial network (GAN), a recurrent neural network (RNN), a long short term memory (LSTM), a neural turing machines (NTM), and a deep residual networks (DRN).

Figure 7:
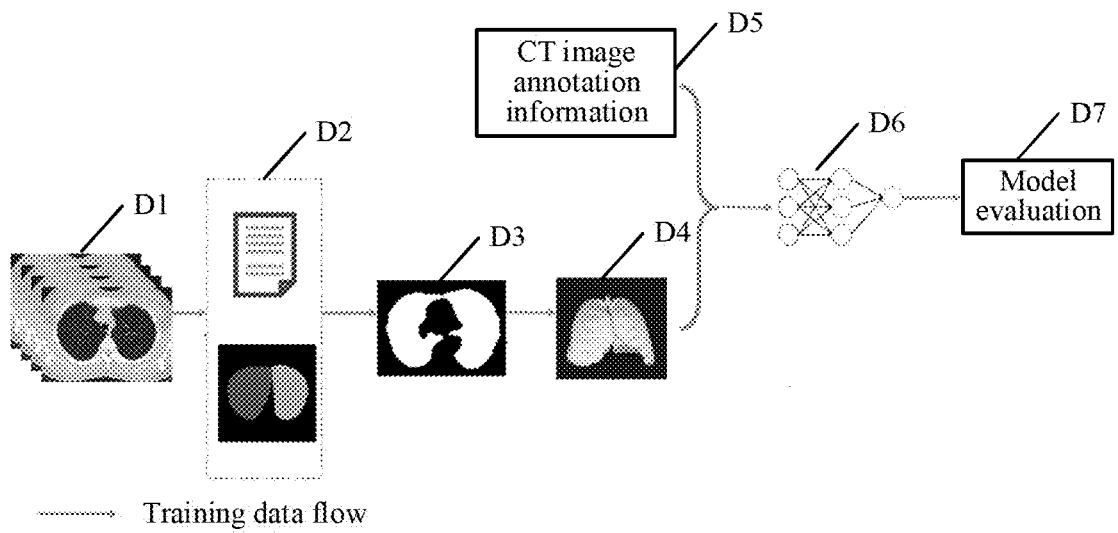
FIG. 7 is a schematic flowchart of training a medical image recognition model according to an exemplary embodiment of the present disclosure.

For ease of description, FIG. 7 is a schematic flowchart of training a medical image recognition model according to an exemplary embodiment of the present disclosure. Specifically, in step D1, a server first acquires a large quantity of original data sets related to lungs through a medical testing device. In step D2, each medical image in the original data set is determined through label information and template matching to obtain a trainable lung image. In step D3, a lung area in the trainable lung image is segmented and extracted. In step D4, image interpolation and normalization are performed on the segmented and extracted lung area. In step D5, additional lung image annotation information may further be obtained. The annotation information herein is usually obtained through manual annotation. For example, annotation information obtained after a lung image sample 1 is annotated with "normal", annotation information obtained after a lung image sample 2 is annotated with "emphysema." In step D6, the lung area obtained through processing in step D4 and the annotation information obtained in step D5 are trained, to obtain the medical image recognition model. In step D7, the medical image recognition model is evaluated, to optimize the medical image recognition model.

In an exemplary embodiment of the present disclosure, a to-be-trained medical image sample set is obtained. The medical image sample set includes at least one medical image sample, and each medical image sample carries corresponding annotation information. The annotation information is used for representing the type of the medical image sample. A to-be-trained area corresponding to each medical image sample in the medical image sample set is then extracted. The to-be-trained area is a part of the medical image sample. A medical image recognition model is obtained through training according to the to-be-trained area corresponding to each medical image sample and the corresponding annotation information carried by each medical image sample. In the foregoing manners, a medical image recognition model may be obtained through training, and the model can be used in place of manual annotation, so that the manual annotation costs and time costs can be greatly reduced. In addition, the model may perform training according to actual requirements to optimize an outputted result, which has high fault tolerance than a manually-outputted result.

Optionally, based on the exemplary embodiment corresponding to FIG. 6, in a first exemplary embodiment of the model training method according to the embodiments of this application, before obtaining a to-be-trained medical image sample set, the method may further include the following steps. In a first step, an original medical image set is obtained, where the original medical image set includes at least one original medical image. In a second step, label information of each original medical image in the original medical image set is obtained. The label information includes information associated with the original medical image. In a third step, in a case that the label information of the original medical image satisfies a sample extraction condition, the original medical image is determined as the medical image sample, until the to-be-trained medical image sample set is obtained from the original medical image set.

In an exemplary embodiment, a preprocessing manner of a medical image is described. For both a medical image recognition scenario and a medical image training scenario, first, a medical image that does not meet the requirements of the recognition scenario or the training scenario needs to be eliminated. Specifically, the server first obtains the original medical image set, the original medical image set including at least one original medical image. Next, it needs to be determined whether each original medical image satisfies the training scenario or the recognition scenario. Finally, original medical images that do not satisfy the scenarios are eliminated.

During determination, information comparison may be performed on the original medical image. That is, it is determined whether label information (also referred to as Meta information) corresponding to each original medical image satisfies a sample extraction condition. The label information includes, but is not limited to, a patient identifier, a hospital identifier, a testing device identifier, tested part information, and testing doctor information corresponding to the original medical image. An attribute of the label information defines associated names and value pairs.

For ease of description, Table 1 schematically shows label information in an original medical image set.

TABLE 1

| Original medical image set | Tested part information |
| --- | --- |
| Original medical image 1 | Lung |
| Original medical image 2 | Lung |
| Original medical image 3 | Liver |
| Original medical image 4 | Lung |
| Original medical image 5 | Heart |
| Original medical image 6 | Lung |
| Original medical image 7 | Lung |

As can be seen in Table 1, if an original medical image that needs to be recognized is a lung image, the original medical image 3 and the original medical image 5 may be eliminated from the original medical image set according to the tested part information in the label information.

Certainly, during actual application, if a non-CT image is mixed in the original medical image set, these original medical images also need to be eliminated. Alternatively, the original medical images that are damaged due to a storage problem or the like also need to be eliminated.

Second, in an exemplary embodiment of the present disclosure, after an original medical image set is obtained, label information of each original medical image in the original medical image set needs to be analyzed, and only an original medical image whose label information satisfies a sample extraction condition can be used as a medical image sample. In the foregoing manners, a large quantity of irrelevant original medical images may be filtered out by using the label information, so as to reduce the time costs of training and obtain make purer overall data, thereby improving the quality and effect of model training.

Optionally, based on the exemplary embodiment corresponding to FIG. 6, in a second exemplary embodiment of the model training method according to the embodiments of this application, before obtaining a to-be-trained medical image sample set, the method may further include the following steps. In a first step, an original medical image set is obtained. The original medical image set includes at least one original medical image. In a second step, label information of each original medical image in the original medical image set is obtained, where the label information includes information associated with the original medical image. In a third step, the original medical image is matched with a target medical image in a case that the label information of the original medical image satisfies a sample extraction condition. The target medical image is a preset image template. In a fourth step, in a case that the original medical image is successfully matched with the target medical image, the original medical image is determined as the medical image sample, until the to-be-trained medical image sample set is obtained from the original medical image set.

In an exemplary embodiment, another preprocessing manner of a medical image is described. For both a medical image recognition scenario and a medical image training scenario, first, a medical image that does not meet the requirements of the recognition scenario or the training scenario needs to be eliminated. Specifically, the server first obtains the original medical image set, the original medical image set including at least one original medical image. Next, it needs to be determined whether each original medical image satisfies the training scenario or the recognition scenario. Finally, original medical images that do not satisfy the scenarios are eliminated.

Figure 8:
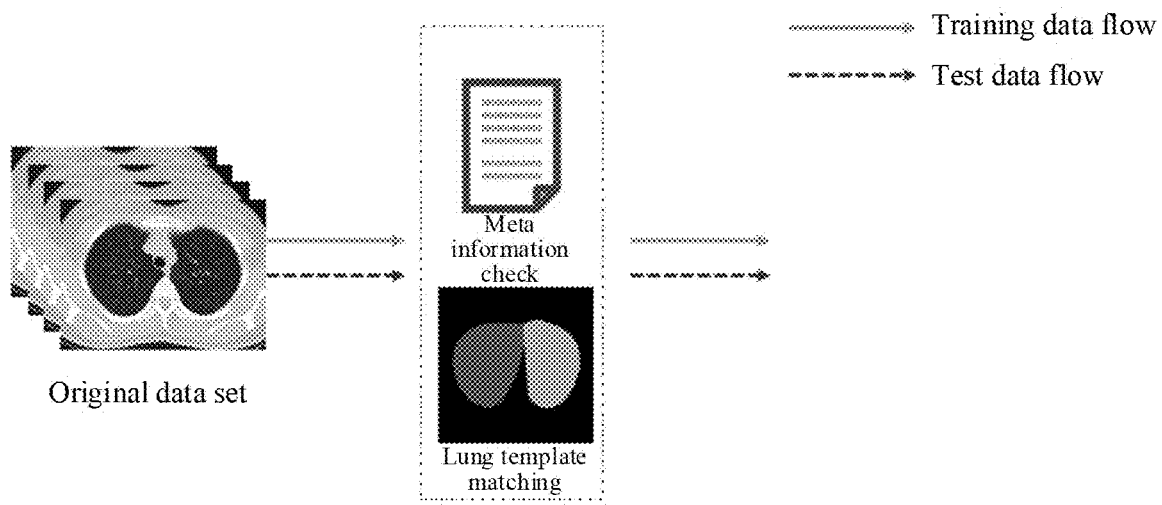
FIG. 8 is a schematic flowchart of determining a medical image sample according to an exemplary embodiment of the present disclosure.

For ease of description, FIG. 8 is a schematic flowchart of determining a medical image sample according to an exemplary embodiment of the present disclosure. As shown in FIG. 8, during determination, information comparison may be performed on the original medical image. That is, it is determined whether label information corresponding to each original medical image satisfies a sample extraction condition (that is, to perform Meta information check). The label information includes, but is not limited to, a patient identifier, a hospital identifier, a testing device identifier, tested part information, and testing doctor information corresponding to the original medical image. Ail attribute of the label information defines associated names and value pairs. In addition, template matching (that is, lung template matching) also needs to be performed on the original medical image. First, a lung image is read, and lung matching is performed according to the template (that is, the target medical image). A normal lung is generally formed by two lung fields (the lung field is a uniform and transparent area of both lungs filled with gas on a chest radiograph) located on the left and right. If the overall shape of a target CT image is successfully matched with the lung template, the image may be determined as a medical image sample, until a to-be-trained medical image sample set is obtained from the original medical image set. By using the two verifications, the validity of the overall input data in subsequent processing may be ensured, and irrelevant data may be prevented from being mixed into the entire system, which is crucial for the overall exception testing classification. After the validity verification is performed, data processing may further be performed.

Certainly, during actual application, if a non-CT image is mixed in the original medical image set, these original medical images also need to be eliminated. Alternatively, the original medical images that are damaged due to a storage problem or the like also need to be eliminated. During verification, the lung area and other areas may be distinguished by training a picture classification model, or it is determined in an image pixel statistical distribution manner whether the original medical image is the lung area.

In an exemplary embodiment of this application, the server first obtains an original medical image set, and then obtains label information of each original medical image in the original medical image set. The server matches the original medical image with a target medical image in a case that the label information of the original medical image satisfies a sample extraction condition, and determines, only in a case that the original medical image is successfully matched with the target medical image, that the original medical image is a medical image sample, until a to-be-trained medical image sample set is obtained from the original medical image set. In the foregoing manners, the matching is performed on the original medical image by using the label information and the template at the same time, and double verification ensures the validity of the overall input data in subsequent processing and prevents irrelevant data from being mixed into the entire system through double verification, which is crucial for the whole exception testing classification, to further reduce the time costs of training, thereby improving the quality and effect of model training.

Optionally, based on the exemplary embodiment corresponding to FIG. 6, in a third exemplary embodiment of the model training method according to the present disclosure, the extracting a to-be-trained area corresponding to each medical image sample in the medical image sample set may include the following steps. In a first step, binarization is performed on each medical image sample in the medical image sample set according to a preset reflected value in order to obtain a binary medical image corresponding to each medical image sample. In a second step, each binary medical image is matched by using a target medical image, to extract a to-be-processed area corresponding to each binary medical image. The target medical image is a preset image template. In a third step, image smoothing is performed on each to-be-processed area, to generate a to-be-extracted outline corresponding to each to-be-processed area. The image smoothing includes performing at least one of an opening operation and a closing operation on each to-be-processed area. In a fourth step, a corresponding to-be-trained area is extracted from each medical image sample by using each to-be-extracted outline.

In an exemplary embodiment, after performing validity verification on the original medical image, the medical image sample may be obtained, where at least one medical image sample may form the to-be-trained medical image sample set. Next, a to-be-trained area (for example, the lung area) further needs to be extracted from each medical image sample. To effectively filter out the noise that may be caused by areas other than the lung field and to make the subsequent model determination more accurate, the calculation amount in addition to the lung field is reduced.

Figure 9:
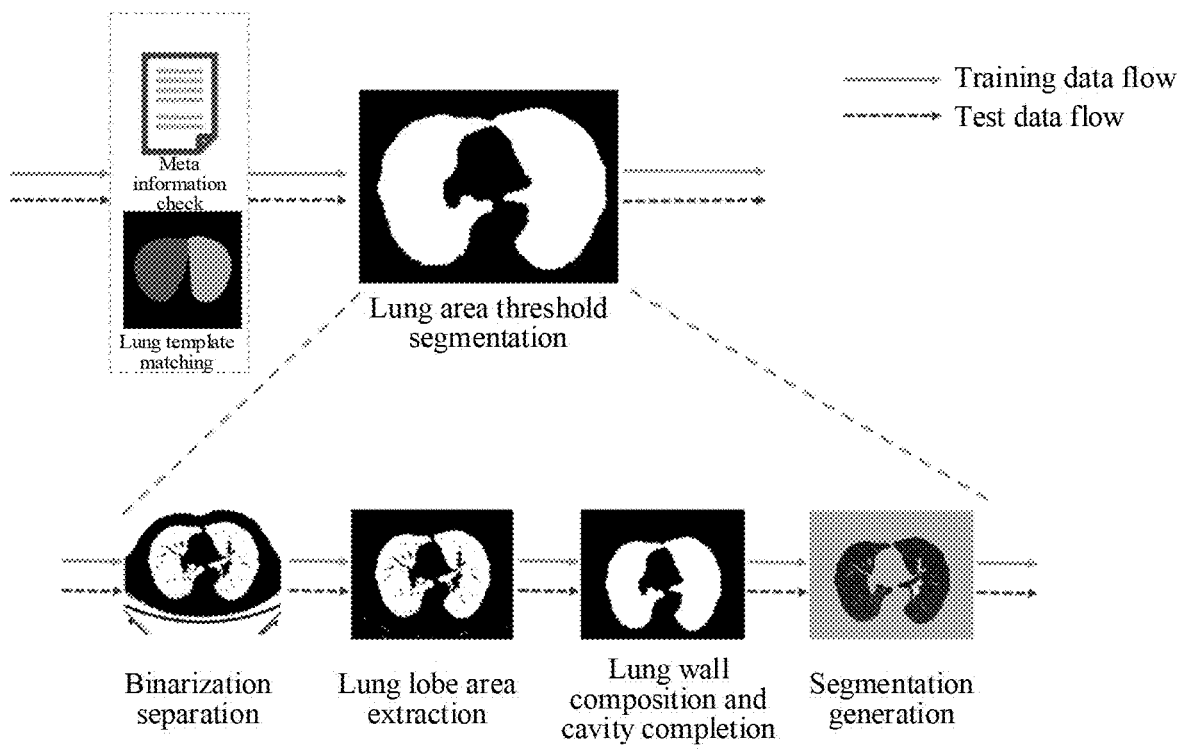
FIG. 9 is a schematic flowchart of extracting a to-be-trained area according to an exemplary embodiment of the present disclosure.

For ease of description, FIG. 9 is a schematic flowchart of extracting a to-be-trained area according to an exemplary embodiment of the present disclosure. As shown in FIG. 9, specifically, an example of extracting a to-be-trained area (or a to-be-recognized area) from the medical image sample is used. First, a binarization separation is performed on the medical image sample. That is, the binarization separation is performed on the medical image sample by using an appropriate thresholding method. Different organs and tissues have different reflected values (for example, CT values), and an approximate outline of a lung may be accurately found from the medical image sample according to the CT values. Assuming that a preset reflected value for a lung is 30 hounsfield units (Hu), a binary medical image with Hu of 30 is extracted.

A CT value is used for reflecting a relative value of a linear attenuation coefficient of a tissue structure in a pixel of a CT image, and a CT value of a substance is equal to a value that is obtained by multiplying a dividing factor by a value obtained by dividing a difference between an attenuation coefficient of the substance and an attenuation coefficient of water by the attenuation coefficient of water. A CT value of a substance reflects the density of the substance, and a higher CT value of a substance indicates a higher density of the substance, that is, $$\text{CT value} = \alpha \times (\mu m - \lambda w)\mu w,$$

Where um is an attenuation coefficient of the substance, $\mu w$ is an attenuation coefficient of water, and $\alpha$ is a dividing factor. When $\alpha$ is 1000, the unit of the CT value is Hu. Different tissues in human body have different attenuation coefficients. Therefore, CT values are different. There are bone tissue, soft tissue, fat, water, and gas in descending order of the CT values, and the CT value of water is around 0 Hu.

During actual application, the binarization may be alternatively performed by using other thresholding methods. For example, an image connectivity may be calculated, and the lung area is determined by calculating two biggest connection quantity. Alternatively, the lung area may be determined by calculating a lung convex area by using methods such as area growth. This is not limited herein.

A lung lobe area is extracted from the binary medical image on which the binarization separation is performed. The extraction manner is to extract a corresponding lung area through a lung CT template (that is, a target medical image used in the second embodiment corresponding to FIG. 6). That is, to match each binary medical image by using the target medical image, to extract a to-be-processed area corresponding to each binary medical image, the target medical image is a preset image template.

The lung area usually has a lung-marking. The lung-marking is dendritic shadows radiating outward from the hilus pulmonis, and is an image formed by pulmonary arteries and pulmonary veins. The bronchus and lymphatics are also included in the lung-marking. A blunt circle on an upper end of the lung is the apex pulmonis, which protrudes upward through the apertura thoracis superior into the root of the neck. A bottom is located on the diaphragm. The faces of opposite ribs and intercostal space are referred to as facies costalis. A face toward the mediastinum is referred to as facies medialis. The bronchus, blood vessel, lymphatics, and nerve exit and entrance of the center of the face is referred to as hilus pulmonis. The structures entering and exiting the hilus pulmonis wrapped in connective tissue are referred to as radix pulmonis. The left lung is divided by an oblique fissure into an upper lung lobe and a lower lung lobe. In addition to the oblique fissure, there is a horizontal fissure that divides the right lung into an upper lung lobe, a middle lung lobe and a lower lung lobe.

Next, smoothing is performed on a to-be-processed area after a lung lobe area is extracted, to obtain a to-be-extracted outline corresponding to the to-be-processed area. This step specifically includes performing an opening operation or a closing operation on each to-be-processed area, or performing an opening operation and a closing operation at the same time. The opening operation may smooth an outline of an image, open a narrow neck and eliminate a thin protrusion. Performing the opening operation on a set A by using a structural element B is defined as:

$$A \circ B = (A \ominus B) \oplus B \quad A \circ B = (A \ominus B) \oplus B.$$

Meaning: Corrode B with A first, and then expand a result with B.

The closing operation also smooths the outline of the image. However, as opposed to the opening operation, the closing operation can bridge narrow gaps and elongated ravines, eliminate small holes, and fill gaps in the contour line. Performing the closing operation on a set A by using a structural element B is defined as:

$$A \cdot B = (A \oplus B) \ominus B \quad A \cdot B = (A \oplus B) \ominus B.$$

Meaning: Expand B with A first, and then corrode a result with B.

Isolated noise points and holes in the to-be-processed area may be removed by using the opening operation and the closing operation, so that the to-be-processed area is smoother.

During actual application, in addition to performing smoothing on the to-be-processed area by using the opening operation and the closing operation, different filtering manners may be used. For example, a mean filter, median filter, Gaussian filter, and/or bilateral filer may be used.

The mean filter is a typical linear filter algorithm in which a template is applied to a target pixel in an image. The template includes adjacent pixels around the target pixel (a filtering template includes 8 pixels with the target pixel as the center, and the target pixel is exclude), and a mean of all pixels in the template is then used to replace an original pixel value. The mean filter is very sensitive to a noise image, especially, an image with big isolated points. Even when there are relatively large differences in an extremely small quantity of points, significant fluctuations of the mean value may be caused.

The median filter is a non-linear smoothing technology, in which the grayscale value of each pixel is set to a median of grayscale values of all pixels in a neighborhood window of the pixel. That is, the value of a center pixel is replaced with a median of all pixel values. The median filter avoids the impact of isolated noise points in an image by choosing a median, and impulse noise can be adequately filtered out. Especially, when the noise is filtered out, an edge of a signal can be protected from being blurred at the same time. These excellent features are not provided by the linear filtering method. In addition, the median filter has a relatively simple algorithm and can be easily implemented by hardware. Therefore, the median filter method is significantly applied to digital signal processing field once being proposed.

The Gaussian filter is a linear smoothing filter, is applicable to the elimination of the Gaussian noise, and is widely applied to a noise reduction process of image processing. Generally, the Gaussian filter is a process of weighted averaging of an entire image. The value of each pixel is obtained by weighted averaging of the value of the pixel and the values of other pixels in the neighborhood. A specific operation of the Gaussian filter is that: using a template (or convolution or mask) to scan every pixel in the image, and using the weighted average grayscale value of the pixels in the neighborhood determined by the template to replace the value of the center pixel of the template. A common reason for the Gaussian filter is that pixels of a real image change slowly in space, so the changes of pixels at adjacent points are not obvious. However, a large pixel difference may be formed between two random points. Based on this point, the Gaussian filter reduces noise while the signal is preserved. Unfortunately, this method is ineffective near the edge because the Gaussian filter may break the edge. However, the Gaussian smoothing filter is still very effective in suppressing noise conforming to normal distribution.

The bilateral filter is a nonlinear filter method, is a compromise process combining spatial proximity and pixel value similarity of an image, and considers both spatial information and grayscale similarity, so as to achieve edge preserving and noise reduction. The bilateral filter is simple, non-iterative, and local. The bilateral filter can provide a method that does not smooth out edges, but bear the expense of a longer processing time. Similar to the Gaussian filter, the bilateral filter may construct a weighted mean according to each pixel and a field thereof. The weighted calculation includes two parts. The weighting manner in the first part is the same as that in Gaussian smoothing. Gaussian weighting is also used in the second part. However, instead of weighting based on spatial distances between the center pixel and other pixels, the weighting is performed based on the brightness difference between the other pixels and the center pixel. The bilateral filter may be considered as Gaussian smoothing in which higher weights are assigned to similar pixels and lower weights are assigned to non-similar pixels, and may also be applied to images classification.

An advantage of the bilateral filter is that it can implement edge preserving. Generally, the Wiener filter or Gaussian filter used in the past to reduce noise has a relatively obvious blurring of edge and a less obvious protective effect on high frequency details. As the name implies, the bilateral filter has one more Gaussian variance than the Gaussian filter. It is a Gaussian filter function based on spatial distribution. Therefore, near the edge, pixels far away from the edge does not affect the pixel value on the edge excessively, thereby ensuring the preservation of pixel values near the edge. However, because excessive high-frequency information is saved, bilateral filters cannot thoroughly filter out high-frequency noise in color images, so that only low-frequency information can be adequately filtered.

A corresponding to-be-trained area is extracted from each medical image sample by using each to-be-extracted outline. Specifically, after a to-be-extracted outline is obtained, the to-be-extracted outline is used as an index and is returned to the medical image sample to extract the to-be-trained area (or the to-be-recognized area).

In an exemplary embodiment of the present disclosure, the extracting a to-be-trained area corresponding to each medical image sample in the medical image sample set specifically includes the following steps. In a first step, binarization on each medical image sample in the medical image sample set is performed according to a preset reflected value to obtain a binary medical image corresponding to each medical image sample. Then each binary medical image is matched by using a target medical image to extract a to-be-processed area corresponding to each binary medical image. Image smoothing is performed on each to-be-processed area to generate a to-be-extracted outline corresponding to each to-be-processed area. A corresponding to-be-trained area is extracted from each medical image sample by using each to-be-extracted outline. In the foregoing manners, the to-be-trained area can be extracted from the medical image sample more accurately, so as to reduce a lot of time costs of calculation, to enable the medical image recognition model to focus on the testing of specific areas, and to avoid incorrect information testing, thereby improving model accuracy.

Optionally, based on the exemplary embodiment corresponding to FIG. 6, in a fourth exemplary embodiment of the model training method according to the present disclosure, after the extracting a to-be-trained area corresponding to each medical image sample in the medical image sample set, the method may further include the following steps. In a first step, the to-be-trained area is scaled down in a case that the to-be-trained area is larger than or equal to a first preset area. In a second step, the to-be-trained area is scaled up in a case that the to-be-trained area is smaller than or equal to a second preset area.

In an exemplary embodiment, after the to-be-trained area is obtained through segmentation, interpolation further needs to be performed on the to-be-trained area to enable the model to achieve a better training effect. An objective is to make a unit physical length in each direction of the image in a three-dimensional image in an equal distance state, which facilitates measurement and model calculation.

In an actual case, different medical image samples have different to-be-trained area sizes. For example, a lung image size of a child is generally less than a lung image size of an adult. In this case, a measuring scale is required. For example, one pixel is equal to 1 mm. If the to-be-trained area is larger than or equal to the first preset area, it indicates that the size of the to-be-trained area may be slightly large. In this case, the to-be-trained area needs to be scaled down according to a ratio, to make the length of each pixel in the to-be-recognized area equal to 1 mm to the greatest extent. In contrast, if the to-be-trained area is smaller than or equal to the second preset area, it indicates that the size of the to-be-trained area may be slightly large. In this case, the to-be-trained area needs to be scaled down according to a ratio, to make the length of each pixel in the to-be-recognized area equal to 1 mm to the greatest extent.

A manner of implementing the foregoing image processing is to perform interpolation in a vertical axis (a z axis). In the present disclosure, conventional linear interpolation is used to make unit physical distances of an image in three directions x, y, and z be the same.

The interpolation may include intra-image interpolation and inter-image interpolation. The intra-image interpolation is mainly used for performing enlargement, rotation, and other operations, and generating another image with relatively high resolution according to an image with relatively low resolution. The inter-image interpolation is also referred to as super resolution reconstruction of images in which a plurality of new images are further generated in an image sequence, and may be applied to interpolation between medical image sequence slices and video sequences. The intra-image interpolation is actually an image reconstruction process on a single-frame image. This means the generation of data that is not present in an original image.

The interpolation manners used in this application may be near interpolation, spline interpolation, bilinear interpolation, double square interpolation, bicubic interpolation, and other higher order methods without limitation.

In the nearest interpolation, each original pixel is copied intact and mapped to a plurality of corresponding pixels after expansion. In the method, all information of all original images is preserved while the image is enlarged. The nearest pixel interpolation is relatively easy and can be easily implemented.

The bilinear interpolation has a smoothing function, so that the deficiency of the nearest pixel interpolation can be effectively overcome.

With a relatively large magnification factor, the higher order interpolation such as bicubic interpolation and cubic spline interpolation has a better effect than low order interpolation.

In an exemplary embodiment of this application, the server may further perform, after extracting a to-be-trained area corresponding to each medical image sample in the medical image sample set, corresponding processing on the to-be-trained area. The server may also scale down the to-be-trained area in a case that the to-be-trained area is larger than or equal to a first preset area, and scale up the to-be-trained area in a case that the to-be-trained area is smaller than or equal to a second preset area. In the foregoing manners, the image interpolation may be performed on the to-be-trained area. An image with high resolution may be generated according to an image with low resolution, and is used to restore lost information in the image. Unit physical lengths of the to-be-trained area in all directions in a three-dimensional image are in an equidistant state, to facilitate model measurement and calculation.

Optionally, based on FIG. 6 or the fourth exemplary embodiment corresponding to FIG. 6, in a fifth exemplary embodiment of the model training method according to the present disclosure, after the extracting a to-be-trained area corresponding to each medical image sample in the medical image sample set, the method may further include the following steps. In a first step, a reflected value interval corresponding to each to-be-trained area is obtained. The maximum value of the reflected value interval is a first reflected value, and the minimum value of the reflected value interval is a second reflected value. In a second step, normalization is performed on each to-be-trained area according to the reflected value interval, to obtain a normalized area. In obtaining a medical image recognition model through training according to the to-be-trained area corresponding to each medical image sample and the corresponding annotation information carried by each medical image sample may, a medical image recognition model may be obtained through training according to the normalized area corresponding to each medical image sample and the corresponding annotation information carried by each medical image sample. The normalization on each of the to-be-trained area based on the reflective value interval may be obtained using the following equation:

$$x_{out} = \frac{x - x_{min}}{x_{max} - x_{min}},$$

Where $x_{out}$ represents the normalized area, x represents a pixel value of the to-be-trained area, $x_{max}$ represents the first reflected value, and $x_{min}$ represents the second reflected value.

In an exemplary embodiment, after the to-be-trained area is obtained through segmentation, normalization further needs to be performed on the to-be-trained area to enable the model to achieve a better training effect. An objective is to make all to-be-trained areas to be in a dimensionally unified state, to facilitate measurement and model calculation.

Figure 10:
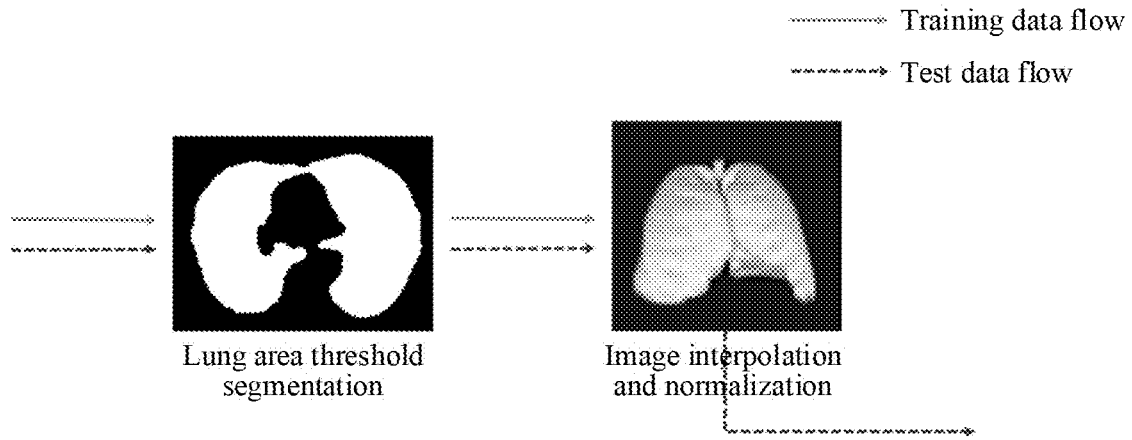
FIG. 10 is a schematic flowchart of adjusting a to-be-trained area according to an exemplary embodiment of the present disclosure.

For ease of description, FIG. 10 is a schematic flowchart of adjusting a to-be-trained area according to an exemplary embodiment of the present disclosure. As shown in FIG. 10, the normalization further needs to be performed on the to-be-trained area according to the reflected value interval after the to-be-trained area is obtained, so as to obtain the normalized area. In a subsequent model training process, the training is performed by using the normalized area after the normalization and the corresponding annotation information carried by each medical image sample, so as to obtain the medical image recognition model.

Specifically, the normalization may integrate all pixels in the image in an interval with a lung window being from −600 Hu to 1024 Hu, and then linearly scale the entire image between 0.0 and 1.0. The window width of the lung window represents a range of a visual CT value, and different content details may be viewed at different window widths. A normalized area may be obtained in an image manner:

$$x_{out} = \frac{x - x_{min}}{x_{max} - x_{min}},$$

Where $x_{out}$ represents the normalized area, x represents a pixel value of the to-be-trained area, $x_{max}$ represents the first reflected value, and $x_{min}$ represents the second reflected value.

An example in which the lung window is from −600 Hu to 1024 Hu is used. $x_{max}$ is 1024 and $x_{min}$ is −600. Assuming that x is 1000, the obtained normalized area of $x_{out}$ is represented as 0.985.

It is to be understood that, the image normalization is a process of performing a series of standard processing changes on an image, to make the image change into a fixed standard form, and the standard image is referred to as a normalized image. Various copy images may be obtained after performing some processing and attacks on an original image, a standard image of the same form can be obtained after the image normalization of the same parameters is performed on the images.

Image normalization uses invariant moments of images to find a set of parameters to make it possible to eliminate the impact of other transformation functions on image transformation, and transforms the original image to the corresponding unique standard form (The image of the standard form is invariant to affine transformations such as translation, rotation, and scaling).

A basic operation principle of a moment-based image normalization technology is that, first, a parameter of a transformation function is determined by using a moment invariant to affine transformation in the image, the original image is then transformed into an image (the image is irrelevant to the affine transformation) of a standard form by using the transform function determined according to the parameter. Generally, a moment-based image normalization process includes four steps, that is, coordinate centralization, x-shearing normalization, scaling normalization, and rotation normalization. The image normalization enables the image to resist attacks of geometric transformation, and invariants in the image can be found, so as to know that the images are the same or belong to one series.

The normalization is a manner of simplifying calculation. That is, to transform a dimensional expression into a dimensionless expression through transformation, so that the expression become scalar. Objectives are as follows: First, it is avoided that input variables with different physical significances and dimensions cannot be equally used. Second, a sigmoid function is usually used as a transformation function in a neural network, and the normalization can prevent neuron output saturation caused by an excessively large absolute value of net input. Third, it is ensured that small values in the output data are not swallowed (or lost).

Causes of normalization in neural networks are specifically that, the normalization is to accelerate the convergence of a training network, and the normalization may not be skipped. A specific function of the normalization is to summarize and unify the statistical distribution of samples. Normalization between 0 and 1 is statistical probability distribution. For both modeling and calculation, the same basic unit of measurement is first required. A neural network is used for training (probability calculation) and prediction based on the statistical probability of a sample in an event. Normalization is the same statistical probability distribution between 0 and 1. When input signals of all samples are positive, weights connected to the neurons in a first hidden layer can only increase or decrease at the same time, leading to a slow learning speed. In order to avoid this case and speed up network learning, the input signals may be normalized, so that a mean of the input signals of all the samples is close to 0 or very small compared with a standard deviation of the input signals. The normalization is performed because the value of the sigmoid function is between 0 and 1, and an output of the last node of the network is also between 0 and 1. Therefore, the normalization is often performed on the output of the sample.

The linear normalization may increase or reduce the length or width of an original image, and preserve linear nature of the image. Sometimes, feature block images may not be in a required form. In this case, the positions of the image centers need to be appropriately corrected after cutting to ensure that the positions are the same. Therefore, the nonlinear normalization technology is used.

Advantages of the image normalization include that a standard mode is obtained through conversion, to prevent the impact of affine transformation, that the impact of the geometric transformation is reduced, and that the gradient descent is accelerated to find the optimal solution.

In an exemplary embodiment of the present disclosure, after extracting a to-be-trained area corresponding to each medical image sample in the medical image sample set, to enable the model to achieve a better training effect, the server may further obtain a reflected value interval corresponding to each to-be-trained area, and perform normalization on each to-be-trained area according to the reflected value interval, so as to obtain a normalized area. In the foregoing manners, the normalization is performed on the to-be-trained areas, and the entire to-be-trained area is linearly scaled between 0 to 1, and a dimensional expression is changed into a dimensionless expression, so that the images corresponding to the to-be-trained areas are in a unified state, to facilitate the data processing and make the calculation of data more convenient and effective.

Optionally, based on the exemplary embodiment corresponding to FIG. 6, in a sixth exemplary embodiment of the model training method according to the present disclosure, the obtaining a medical image recognition model through training according to the to-be-trained area corresponding to each medical image sample and the corresponding annotation information carried by each medical image sample may include the following steps. In a first step, the to-be-trained area corresponding to each medical image sample and the corresponding annotation information carried by each medical image sample is trained through a residual network resnet-18 structure by using a stochastic gradient descent (SGD) algorithm, to obtain a training result. In a second step, a plurality of authentication set loss values is obtained according to the training result. In a third step, the medical image recognition model is obtained according to the plurality of authentication set loss values.

In an exemplary embodiment, after the processed medical image sample is obtained, a classification network training of abnormal testing may be performed by using the corresponding annotation information carried by each medical image sample. The medical image recognition model classifies various images according to annotation information of different images into symptoms such as bronchiectasia, emphysema, pulmonary atelectasis, exudation, consolidation, proliferation, fibrosis, calcification, lump, node, hole, cavity, pleural effusion, hydropneumothorax, and pneumothorax. The medical image recognition model is optimized through the residual network resnet-18 structure in a deep learning network by using the SGD. Finally, a model evaluation is performed, and model results that satisfy indices are selected and saved.

Figure 11:
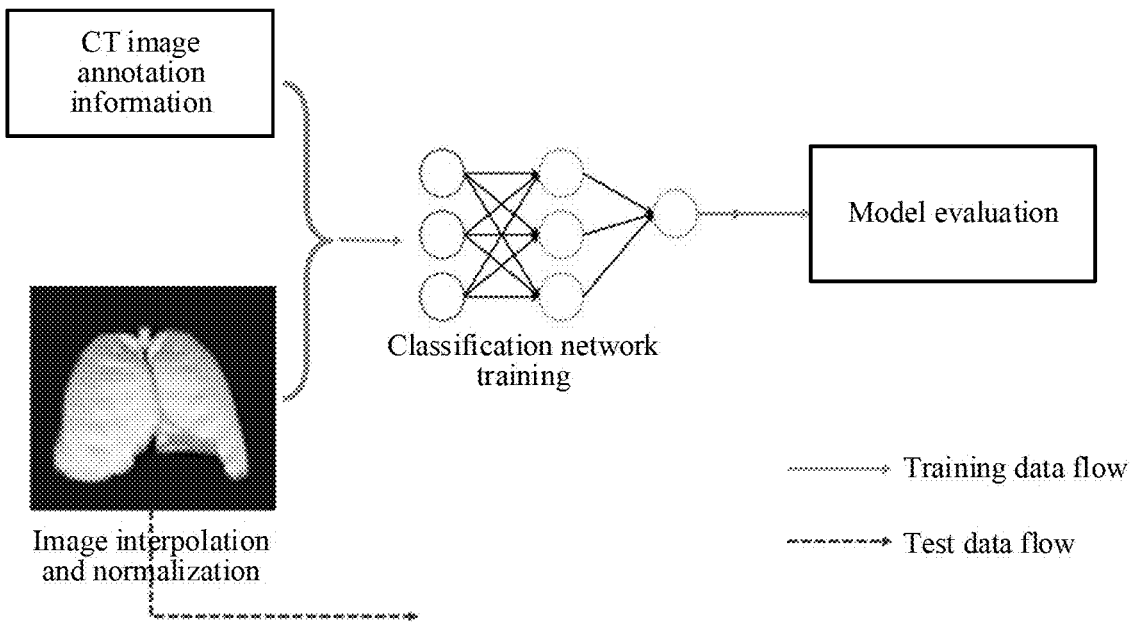
FIG. 11 is a schematic flowchart of establishing a medical image recognition model according to an exemplary embodiment of the present disclosure.

For ease of description, FIG. 11 is a schematic flowchart of establishing a medical image recognition model according to an exemplary embodiment of the present disclosure. As shown in FIG. 11, a deep learning neural network, that is, the residual network resnet-18 structure is established first. The optimization of the residual function is easier, so as to greatly deepen a quantity of network layers, and the residual learning resolves a degradation problem caused by the increase of network depth, so that the optimization of the residual network is easier, and convergence is faster. In this application, the resnet-18 structure is used for deep learning, which has higher cost performance.

Next, the function SGD needs to be trained and optimized, and a learning rate and a quantity of times of iteration need to be set. A large learning rate indicates faster convergence. An authentication set loss value corresponding to each group of authentication sets may be obtained according to a training result, and the minimum value is selected as the optimal solution, so as to deduce a corresponding model.

A simple function of two variables is used as an example. If an extremum of the function of two variables needs to be found, the derivative of this function of two variables is calculated first. The derivative is made zero to find the value of an independent variable. The independent variable is then substituted into the function, and the extremum of the function may then be obtained. The SGD algorithm is to resolve the optimal value problem of a target function of a plurality of variables in deep learning, and there is a plurality of variant algorithms of the algorithm. Therefore, in the deep learning, to resolve actual problems, a model first needs to be established, and a target function is then determined. The target function is usually an error between a network output value and a target. There is a plurality of types of errors. For example, conventional errors are difference of square and cross entropy. An objective of training a model is to minimize the target function. A deep neural network has a large quantity of parameters. Therefore, the target function is usually a nonlinear function containing a plurality of parameters. The SGD algorithm is used to update the parameters of the nonlinear function. Specifically, the steps include a first step, in which network parameters are initialized, where generally, the weight is initialized to a Gaussian distribution random value with a mean of 0 and a variance of 0.01, and the bias is uniformly initialized to 0. In a second step, the parameters are substituted into the network to calculate a feedforward output value, to obtain a target function value according to the existing target label. In a third step, the gradient of each parameter is calculated according to the target function value and a tree structure formed by each parameter and the target function by using the backward propagation algorithm. In a fourth step, the learning rate size is set (as a quantity of iterative steps increases, the learning rate usually decreases gradually, which can effectively avoid the occurrence of error shock in training), and the parameters are updated. The most common updating method is: new parameter=old parameter−learning rate×gradient. In a fifth step, the second through fourth steps are repeated until the network converges, so as to determine the model.

During actual application, in addition to performing model training by using the resnet-18 structure, classification further needs to be performed by using a plurality of types of model structures based on the convolutional neural network (CNN). The essence of all of the model structures is feature extraction, feature fusion, and feature discrimination of the neural network on an image.

In addition, the feature extraction may be alternatively performed by using an image processing algorithm such as a scale-invariant feature transform (SIFT) or a histogram of oriented gradient (HOG), and the classification processing may be performed by using a classifier such as a support vector machine (SVM), a multi-layer perceptron (MLP) or an adaboost algorithm. This is not limited herein.

In addition, in an exemplary embodiment of the present disclosure, a manner of obtaining a medical image recognition model through training is described. Specifically, a to-be-trained area corresponding to each medical image sample and corresponding annotation information carried by each medical image sample are trained by using SGD and through the resnet-18 structure, to obtain a training result. A plurality of authentication set loss values are then obtained according to the training result, and the medical image recognition model is determined according to the plurality of authentication set loss values. In the foregoing manners, the use of SGD to update parameters can ensure the performance of model training, and the resnet-18 structure has an adequate price-performance ratio, which also facilitate the optimization of model training performance.

Optionally, based on the sixth exemplary embodiment corresponding to FIG. 6, in a seventh exemplary embodiment of the model training method according to the present disclosure, the determining a medical image recognition model according to the plurality of authentication set loss values may include the following steps. In a first step, a target authentication set loss value is determined from the plurality of authentication set loss values. The target authentication set loss value is the minimum value in the plurality of authentication set loss values. In a second step, a training result corresponding to the target authentication set loss value is determined as the medical image recognition model.

In an exemplary embodiment, a manner of optimizing the medical image recognition model is described. A server needs to determine a target authentication set loss value from a plurality of authentication set loss values, the target authentication set loss value being the minimum value in the plurality of authentication set loss values, and determine a training result corresponding to the target authentication set loss value as the medical image recognition model.

Specifically, a target function is preset before the model is trained, and training sets are kept on the target function as much as possible. However, in fact, it may be not possible to fit all the training sets on the target function. Therefore, it is necessary to adjust and modify the target function repeatedly. When a distance between the training set and the target function is minimum, it indicates that a fitting effect is optimized. Therefore, a target function in the minimum value state may be used as a final training result, so as to obtain the medical image recognition model.

The fitting is connecting a series of points on a plane with a smooth curve. Because there are an infinite quantity of possibilities for this curve, there are various fitting ways. Many factors affect the curve fitting, resulting in an adequate or an inadequate fitting effect. Several methods may be used in order to improve the fitting quality. For example, selection of a model may be the main factor, and various models are tried to perform data fitting and comparison. Data processing may also be useful to preprocess data before fitting, including transforming response data and removing points with obvious errors. A proper fit also entails the capability to process a case that a singularity occurs to make the prediction tend towards infinity. The data may be decomposed into a plurality of subsets, and different curve fittings are used for different subsets. Complex problems may also be preferentially solved by evolution, in which a small quantity of independent variables in a problem are solved first. The solution to the lower order problem is usually used as the starting point of the solution to the higher order problem by approximate mapping.

Further, a manner of optimizing the medical image recognition model is described in an exemplary embodiment of the present disclosure, that is, a server first determines a target authentication set loss value from a plurality of authentication set loss values, the target authentication set loss value being the minimum value in the plurality of authentication set loss values. Then the server determines a training result corresponding to the target authentication set loss value as the medical image recognition model. In the foregoing manners, when the minimum value in the authentication set loss value is obtained, it indicates that at present the model better satisfies an actual case, that is, is closer to the reality of the model. Therefore, an optimized medical image recognition model is obtained, and model results that satisfy indices are selected and saved.

Optionally, based on the exemplary embodiment corresponding to FIG. 6, in an eighth exemplary embodiment of the model training method according to the present disclosure, after the obtaining a medical image recognition model through training according to the to-be-trained area corresponding to each medical image sample and the corresponding annotation information carried by each medical image sample, the method may further include the following steps. In a first step, a to-be-recognized medical image set is obtained. The to-be-recognized medical image set includes at least one to-be-recognized medical image. In a second step, a to-be-recognized area corresponding to each to-be-recognized medical image in the to-be-recognized medical image set is extracted. The to-be-recognized area is a part of the to-be-recognized medical image. In a third step, a recognition result of each to-be-recognized area is determined through the medical image recognition model. The recognition result is used for representing the type of the to-be-recognized medical image.

Figure 12:
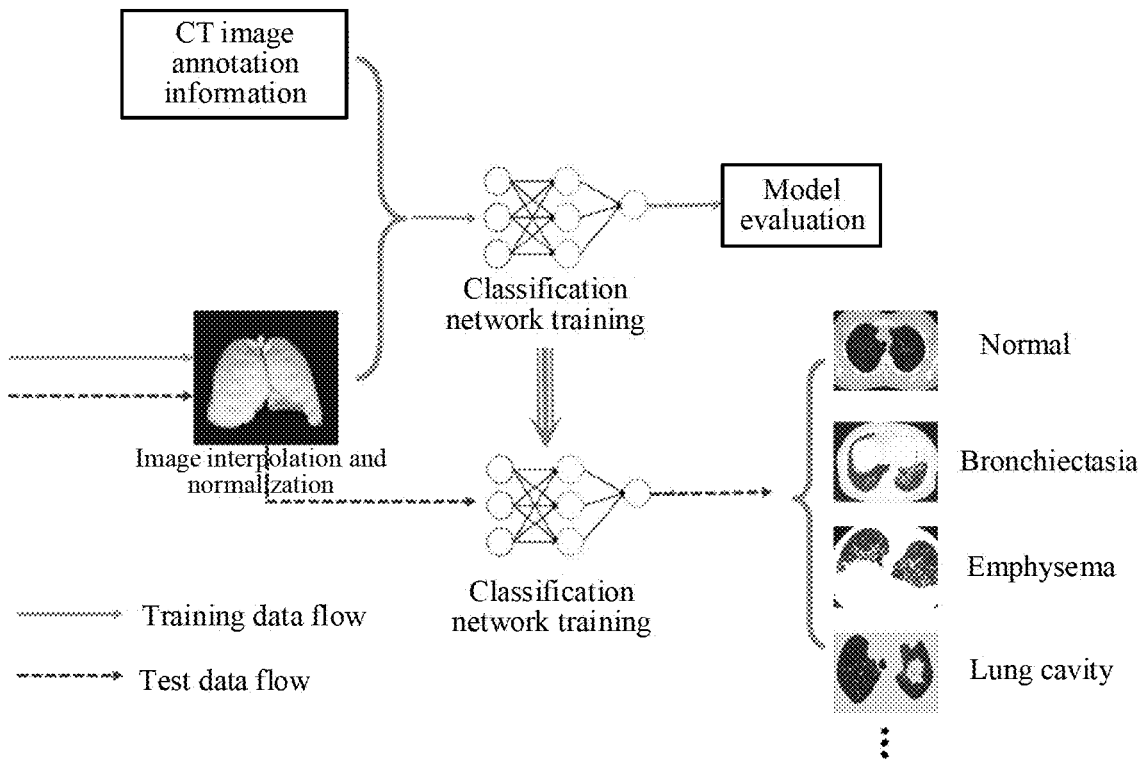
FIG. 12 is a schematic flowchart of loading a medical image recognition model according to an exemplary embodiment of the present disclosure.

In an exemplary embodiment, a manner of recognizing a medical image by using a medical image recognition model is described. A lung image is used as an example for description. FIG. 12 is a schematic flowchart of loading a medical image recognition model according to an embodiment of this application. As shown in FIG. 12. In a scenario of medical image recognition, a server first obtains a to-be-recognized medical image set. The to-be-recognized medical image set may only include one to-be-recognized medical image or may include a plurality of to-be-recognized medical images. Next, the server may perform feature extraction on each to-be-recognized medical image, so as to obtain a to-be-recognized area. The process of feature extraction includes performing image interpolation and normalization on the to-be-recognized medical image. The server inputs each to-be-recognized area into the medical image recognition model. The medical image recognition model then outputs the recognition result corresponding to each to-be-recognized area. The recognition result may represent the type of the to-be-recognized medical image, for example, "normal", "emphysema", "bronchiectasia" or "calcification".

The medical image recognition model is obtained through training by using a large quantity of medical image samples. Each medical image sample carries corresponding annotation information. For example, annotation information of a lung image sample 1 is "normal", annotation information of a lung image sample 2 is "emphysema", annotation information of a lung image sample 3 is "calcification", and the like. The annotation information herein is usually obtained through manual annotation.

In an exemplary embodiment of the present disclosure, after obtaining the medical image recognition model through training, the server may further use the medical image recognition model to recognize the to-be-recognized medical image set, that is, to first extract a to-be-recognized area corresponding to each to-be-recognized medical image in the to-be-recognized medical image set. The to-be-recognized area is a part of the to-be-recognized medical image. The server then determines a recognition result corresponding to each to-be-recognized area through the medical image recognition model. In the foregoing manners, the medical image recognition model is used in place of manual annotation, so that the manual annotation costs and time costs can be greatly reduced. In addition, the use of the model to recognize a medical image is applicable to a plurality of scenarios, the accuracy of recognition does not vary for different users, and relatively high reliability and accuracy are achieved.

Figure 13:
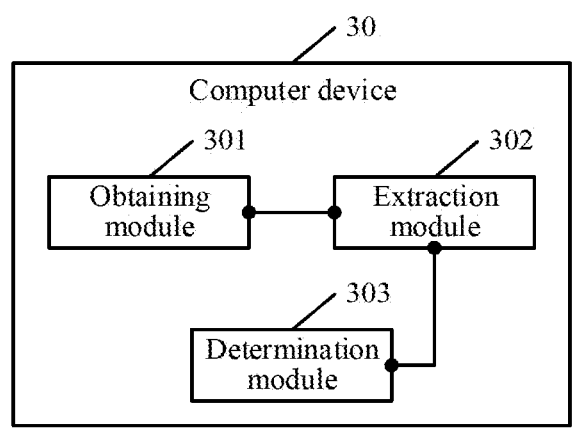
FIG. 13 is a schematic diagram of a computer device according to an exemplary embodiment of the present disclosure.

A computer device corresponding to an exemplary embodiment of the present disclosure is described below in detail. FIG. 13 is a schematic diagram of an exemplary embodiment of a computer device according to the present disclosure. The computer device 30 includes an obtaining module 301, an extraction module 302, and a determination module 303. These modules may be implemented by circuitry, for example.

The obtaining module obtains a to-be-recognized medical image set. The to-be-recognized medical image set including at least one to-be-recognized medical image. The extraction module 302 extracts a to-be-recognized area corresponding to each to-be-recognized medical image in the to-be-recognized medical image set obtained by the obtaining module 301. The to-be-recognized area is a part of the to-be-recognized medical image. The determination module 303 determines, through a medical image recognition model, a recognition result of each to-be-recognized area extracted by the extraction module 302. The medical image recognition model is obtained through training according to a medical image sample set, where the medical image sample set includes at least one medical image sample. Each medical image sample carries corresponding annotation information, and the annotation information is used for representing the type of the medical image sample. The recognition result is used for representing the type of the to-be-recognized medical image.

In an exemplary embodiment, the obtaining module 301 obtains the to-be-recognized medical image set. The to-be-recognized medical image set includes at least one to-be-recognized medical image. The extraction module 302 then extracts a to-be-recognized area corresponding to each to-be-recognized medical image in the to-be-recognized medical image set obtained by the obtaining module 301. The to-be-recognized area is a part of the to-be-recognized medical image. The determination module 303 determines, through a medical image recognition model, a recognition result of each to-be-recognized area extracted by the extraction module 302, the medical image recognition model being obtained through training according to a medical image sample set. The medical image sample set includes at least one medical image sample, and each medical image sample carries corresponding annotation information. The annotation information is used for representing the type of the medical image sample, and the recognition result is used for representing the type of the to-be-recognized medical image.

In an exemplary embodiment of the present disclosure, a medical image recognition method is provided. First, a computer device obtains a to-be-recognized medical image set. The to-be-recognized medical image set includes at least one to-be-recognized medical image. Then a to-be-recognized area corresponding to each to-be-recognized medical image in the to-be-recognized medical image set is extracted. The to-be-recognized area is a part of the to-be-recognized medical image. A recognition result of each to-be-recognized area is determined through a medical image recognition model. The medical image recognition model is obtained through training according to a medical image sample set. The medical image sample set includes at least one medical image sample, and each medical image sample carries corresponding annotation information. The annotation information is used for representing the type of the medical image sample, and the recognition result is used for representing the type of the to-be-recognized medical image. In the foregoing manners, the medical image recognition model is used in place of manual annotation, so that the manual annotation costs and time costs can be greatly reduced. In addition, the use of the model to recognize a medical image is applicable to a plurality of scenarios, the accuracy of recognition does not vary for different users, and relatively high reliability and accuracy are achieved.

Figure 14:
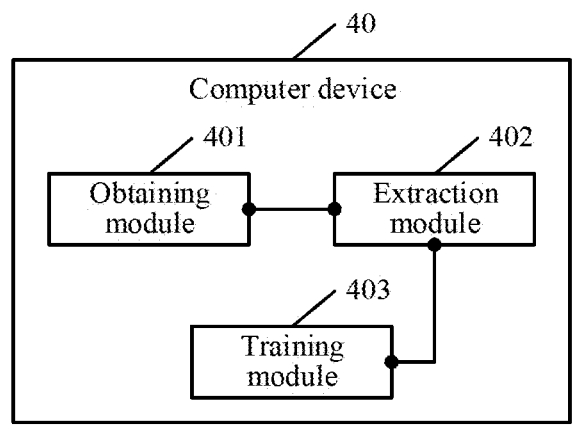
FIG. 14 is a schematic diagram of a computer device according to an exemplary embodiment of the present disclosure.

A computer device corresponding to an exemplary embodiment of this application is described below in detail. FIG. 14 is a schematic diagram of a computer device according to an exemplary embodiment of the present disclosure. The computer device 40 includes an obtaining module 401, an extraction module 402, and a training module 403. These modules may be implemented by circuitry, for example.

The obtaining module 401 obtains a to-be-trained medical image sample set. The medical image sample set includes at least one medical image sample, and each medical image sample carries corresponding annotation information. The annotation information is used for representing the type of the medical image sample. The extraction module 402 extracts a to-be-trained area corresponding to each medical image sample in the medical image sample set obtained by the obtaining module 401. The to-be-trained area is a part of the medical image sample. The training module 403 obtains a medical image recognition model through training according to the to-be-trained area corresponding to each medical image sample extracted by the extraction module and the corresponding annotation information carried by each medical image sample.

In an exemplary embodiment, the obtaining module 401 obtains a to-be-trained medical image sample set, where the medical image sample set includes at least one medical image sample. Each medical image sample carries corresponding annotation information, and the annotation information is used for representing the type of the medical image sample. The extraction module 402 then extracts a to-be-trained area corresponding to each medical image sample in the medical image sample set obtained by the obtaining module 401, where the to-be-trained area is a part of the medical image sample. The training module 403 obtains a medical image recognition model through training according to the to-be-trained area corresponding to each medical image sample extracted by the extraction module and the corresponding annotation information carried by each medical image sample.

In an exemplary embodiment of the present disclosure, a to-be-trained medical image sample set is obtained, where the medical image sample set includes at least one medical image sample. Each medical image sample carries corresponding annotation information, and the annotation information is used for representing the type of the medical image sample. A to-be-trained area corresponding to each medical image sample in the medical image sample set is then extracted, where the to-be-trained area is a part of the medical image sample. A medical image recognition model is obtained through training according to the to-be-trained area corresponding to each medical image sample and the corresponding annotation information carried by each medical image sample. In the foregoing manners, a medical image recognition model may be obtained through training, and the model can be used in place of manual annotation, so that the manual annotation costs and time costs can be greatly reduced. In addition, the model may perform training according to actual requirements to optimize an outputted result, which has high fault tolerance than a manually-outputted result.

Figure 15:
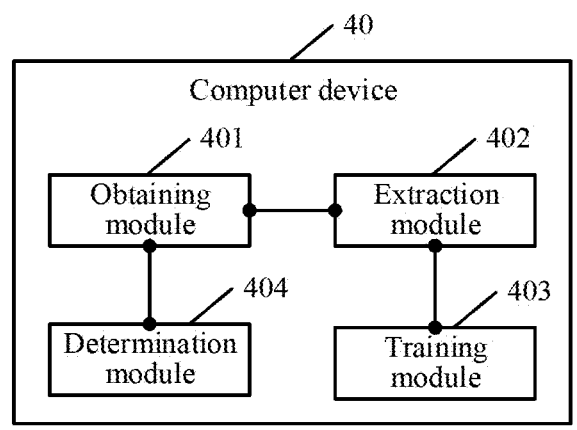
FIG. 15 is a schematic diagram of a computer device according to an exemplary embodiment of the present disclosure.

Optionally, based on an exemplary embodiment corresponding to FIG. 14, referring to FIG. 15, in another exemplary embodiment of the computer device 40 provided according to the present disclosure, the computer device 40 further includes a determination module 404, which may also be implemented by circuitry.

The obtaining module 401 is further configured to obtain an original medical image set before obtaining the to-be-trained medical image sample set, the original medical image set including at least one original medical image.

The obtaining module 401 is further configured to obtain label information of each original medical image in the original medical image set, the label information including information associated with the original medical image.

The determination module 404 is configured to determine, in a case that the label information of the original medical image obtained by the obtaining module 401 satisfies a sample extraction condition, that the original medical image is the medical image sample, until the to-be-trained medical image sample set is obtained from the original medical image set.

In an exemplary embodiment of this application, after an original medical image set is obtained, label information of each original medical image in the original medical image set needs to be analyzed, and only an original medical image whose label information satisfies a sample extraction condition can be used as a medical image sample. In the foregoing manners, a large quantity of irrelevant original medical images may be filtered out by using the label information, so as to reduce the time costs of training and obtain make purer overall data, thereby improving the quality and effect of model training.

Figure 16:
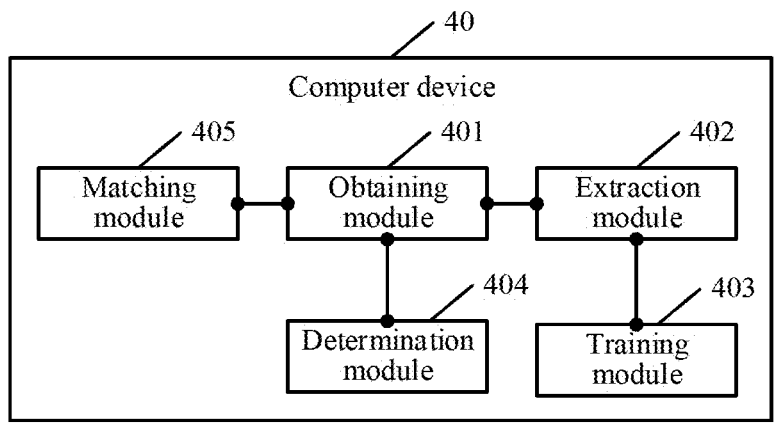
FIG. 16 is a schematic diagram of a computer device according to an exemplary embodiment of the present disclosure.

Optionally, based on the exemplary embodiment corresponding to FIG. 14, referring to FIG. 16, in another exemplary embodiment of the computer device 40 according to the present disclosure, the computer device 40 further includes a determination module 404 and a matching module 405, both of which may be implemented by circuitry.

The obtaining module 401 is further configured to obtain an original medical image set, the original medical image set including at least one original medical image.

The obtaining module 401 is further configured to obtain label information of each original medical image in the original medical image set, the label information including information associated with the original medical image.

The matching module 405 is configured to match the original medical image with a target medical image in a case that the label information of the original medical image obtained by the obtaining module 401 satisfies a sample extraction condition, the target medical image being a preset image template.

The determination module 404 is configured to determine, in a case that the original medical image obtained by the obtaining module 401 is successfully matched with the target medical image, that the original medical image is the medical image sample, until the to-be-trained medical image sample set is obtained from the original medical image set.

In an exemplary embodiment of this application, the computer device first obtains an original medical image set, and then obtains label information of each original medical image in the original medical image set. The computer matches the original medical image with a target medical image in a case that the label information of the original medical image satisfies a sample extraction condition, and determines, only in a case that the original medical image is successfully matched with the target medical image, that the original medical image is a medical image sample, until a to-be-trained medical image sample set is obtained from the original medical image set. In the foregoing manners, the matching is performed on the original medical image by using the label information and the template at the same time, and double verification ensures the validity of the overall input data in subsequent processing and prevents irrelevant data from being mixed into the entire system through double verification, which is crucial for the whole exception testing classification, so as to further reduce the time costs of training, thereby improving the quality and effect of model training.

Optionally, based on another exemplary embodiment corresponding to FIG. 14, the extraction module 402 performs binarization on each medical image sample in the medical image sample set according to a preset reflected value to obtain a binary medical image corresponding to each medical image sample, and then matches each binary medical image by using a target medical image to extract a to-be-processed area corresponding to each binary medical image. The target medical image is a preset image template. The extraction module 402 performs image smoothing on each to-be-processed area to generate a to-be-extracted outline corresponding to each to-be-processed area. The image smoothing includes performing at least one of an opening operation and a closing operation on each to-be-processed area. The extraction module 402 extracts a corresponding to-be-trained area from each medical image sample by using each to-be-extracted outline.

In addition, in an exemplary embodiment of the present disclosure, the extracting a to-be-trained area corresponding to each medical image sample in the medical image sample set specifically includes the following steps. First binarization on each medical image sample in the medical image sample set is performed according to a preset reflected value to obtain a binary medical image corresponding to each medical image sample. Next each binary medical image is matched by using a target medical image to extract a to-be-processed area corresponding to each binary medical image. Image smoothing on to-be-processed area is then performed to generate a to-be-extracted outline corresponding to each to-be-processed area. A corresponding to-be-trained area is extracted from each medical image sample by using each to-be-extracted outline. In the foregoing manners, the to-be-trained area can be extracted from the medical image sample more accurately, so as to reduce a lot of time costs of calculation, to enable the medical image recognition model to focus on the testing of specific areas, and to avoid incorrect information testing, thereby improving model accuracy.

Figure 17:
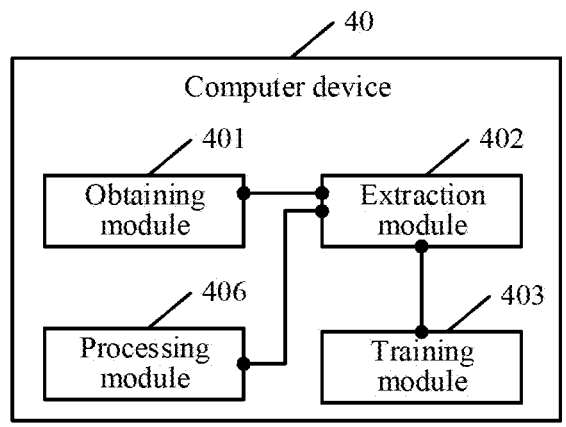
FIG. 17 is a schematic diagram of a computer device according to an exemplary embodiment of the present disclosure.

Optionally, based on the exemplary embodiment corresponding to FIG. 14, referring to FIG. 17, in another exemplary embodiment of the computer device 40 according to the present disclosure, the computer device 40 further includes a processing module 406, which may be implemented by circuitry.

The processing module 406 is configured to scale down, after a to-be-trained area corresponding to each medical image sample in the medical image sample set is extracted by the extraction module 402, the to-be-trained area in a case that the to-be-trained area is larger than or equal to a first preset area.

The processing module 406 is configured to scale up the to-be-trained area in a case that the to-be-trained area extracted by the extraction module 402 is smaller than or equal to a second preset area.

In an exemplary embodiment of the present disclosure, the computer device 40 may further perform, after extracting a to-be-trained area corresponding to each medical image sample in the medical image sample set, corresponding processing on the to-be-trained area. The computer device may then scale down the to-be-trained area in a case that the to-be-trained area is larger than or equal to a first preset area, and scale up the to-be-trained area in a case that the to-be-trained area is smaller than or equal to a second preset area. In the foregoing manners, the image interpolation may be performed on the to-be-trained area. An image with high resolution may be generated according to an image with low resolution, and is used to restore lost information in the image. Unit physical lengths of the to-be-trained area in all directions in a three-dimensional image are in an equidistant state, to facilitate model measurement and calculation.

Optionally, based on the exemplary embodiment corresponding to FIG. 14 or FIG. 17, in another exemplary embodiment of the computer device 40 according to the present disclosure, the obtaining module 401 is further configured to obtain a reflected value interval corresponding to each to-be-trained area after the extraction module 402 extracts the to-be-trained area corresponding to each medical image sample in the medical image sample set. The maximum value of the reflected value interval is a first reflected value, and the minimum value of the reflected value interval is a second reflected value. The processing module 406 is further configured to perform normalization on each to-be-trained area according to the reflected value interval obtained by the obtaining module 401, to obtain a normalized area. The training module 403 is specifically configured to obtain the medical image recognition model through training according to the normalized area corresponding to each medical image sample and the corresponding annotation information carried by each medical image sample. The processing module 406 is specifically configured to obtain the normalized area in the following manner:

$$x_{out} = \frac{x - x_{min}}{x_{max} - x_{min}},$$

Where $x_{out}$ represents the normalized area, x represents a pixel value of the to-be-trained area, $x_{max}$ represents the first reflected value, and $x_{min}$ represents the second reflected value.

In an exemplary embodiment of the present disclosure, after extracting a to-be-trained area corresponding to each medical image sample in the medical image sample set, to enable the model to achieve a better training effect, the computer device 40 may further obtain a reflected value interval corresponding to each to-be-trained area, and perform normalization on each to-be-trained area according to the reflected value interval, so as to obtain a normalized area. In the foregoing manners, the normalization is performed on the to-be-trained areas, and the entire to-be-trained area is linearly scaled between 0 to 1, and a dimensional expression is changed into a dimensionless expression, so that the images corresponding to the to-be-trained areas are in a unified state, to facilitate the data processing and make the calculation of data more convenient and effective.

Optionally, based on the exemplary embodiment corresponding to FIG. 14, in another exemplary embodiment of the computer device 40 according to the present disclosure, the training module 403 trains the to-be-trained area corresponding to each medical image sample and the corresponding annotation information carried by each medical image sample through a residual network resnet-18 structure by using an SGD algorithm, to obtain a training result, obtains a plurality of authentication set loss values according to the training result, and determines the medical image recognition model according to the plurality of authentication set loss values.

In addition, in an exemplary embodiment of the present disclosure, a manner of obtaining a medical image recognition model through training is described. Specifically, a to-be-trained area corresponding to each medical image sample and corresponding annotation information carried by each medical image sample are trained by using SGD and through the resnet-18 structure, to obtain a training result. A plurality of authentication set loss values are then obtained according to the training result, and the medical image recognition model is determined according to the plurality of authentication set loss values. In the foregoing manners, the use of SGD to update parameters can ensure the performance of model training, and the resnet-18 structure has an adequate price-performance ratio, which also facilitate the optimization of model training performance.

Optionally, based on the exemplary embodiment corresponding to FIG. 14, in another exemplary embodiment of the computer device 40 according to the present disclosure, the determination module 404 determines a target authentication set loss value from the plurality of authentication set loss values, the target authentication set loss value being the minimum value in the plurality of authentication set loss values, and determines a training result corresponding to the target authentication set loss value as the medical image recognition model.

Further, a manner of optimizing the medical image recognition model is described in an exemplary embodiment of the present disclosure. That is, a computer device first determines a target authentication set loss value from a plurality of authentication set loss values. The target authentication set loss value is the minimum value in the plurality of authentication set loss values, the computer device then determines a training result corresponding to the target authentication set loss value as the medical image recognition model. In the foregoing manners, when the minimum value in the authentication set loss value is obtained, it indicates that at present the model better satisfies an actual case, that is, is closer to the reality of the model. Therefore, an optimized medical image recognition model is obtained, and model results that satisfy indices are selected and saved.

Optionally, based on the exemplary embodiment corresponding to FIG. 14, in another exemplary embodiment of the computer device 40 according to the present disclosure, the obtaining module 401 obtains a to-be-recognized medical image set after the medical image recognition model is obtained by the training module 403 through training according to the to-be-trained area corresponding to each medical image sample and the corresponding annotation information carried by each medical image sample. The to-be-recognized medical image set includes at least one to-be-recognized medical image. The extraction module 402 extracts a to-be-recognized area corresponding to each to-be-recognized medical image in the to-be-recognized medical image set obtained by the obtaining module 401. The to-be-recognized area is a part of the to-be-recognized medical image. The determination module 404 determines, through the medical image recognition model, a recognition result of each to-be-recognized area extracted by the extraction module 402. The recognition result is used for representing the type of the to-be-recognized medical image.

In an exemplary embodiment of the present disclosure, after obtaining the medical image recognition model through training, the computer device may further use the medical image recognition model to recognize the to-be-recognized medical image set, that is, to extract a to-be-recognized area corresponding to each to-be-recognized medical image in the to-be-recognized medical image set. The to-be-recognized area is a part of the to-be-recognized medical image. The computer device determines a recognition result corresponding to each to-be-recognized area through the medical image recognition model. In the foregoing manners, the medical image recognition model is used in place of manual annotation, so that the manual annotation costs and time costs can be greatly reduced. In addition, the use of the model to recognize a medical image is applicable to a plurality of scenarios, the accuracy of recognition does not vary for different users, and high reliability and credibility are achieved.

Figure 18:
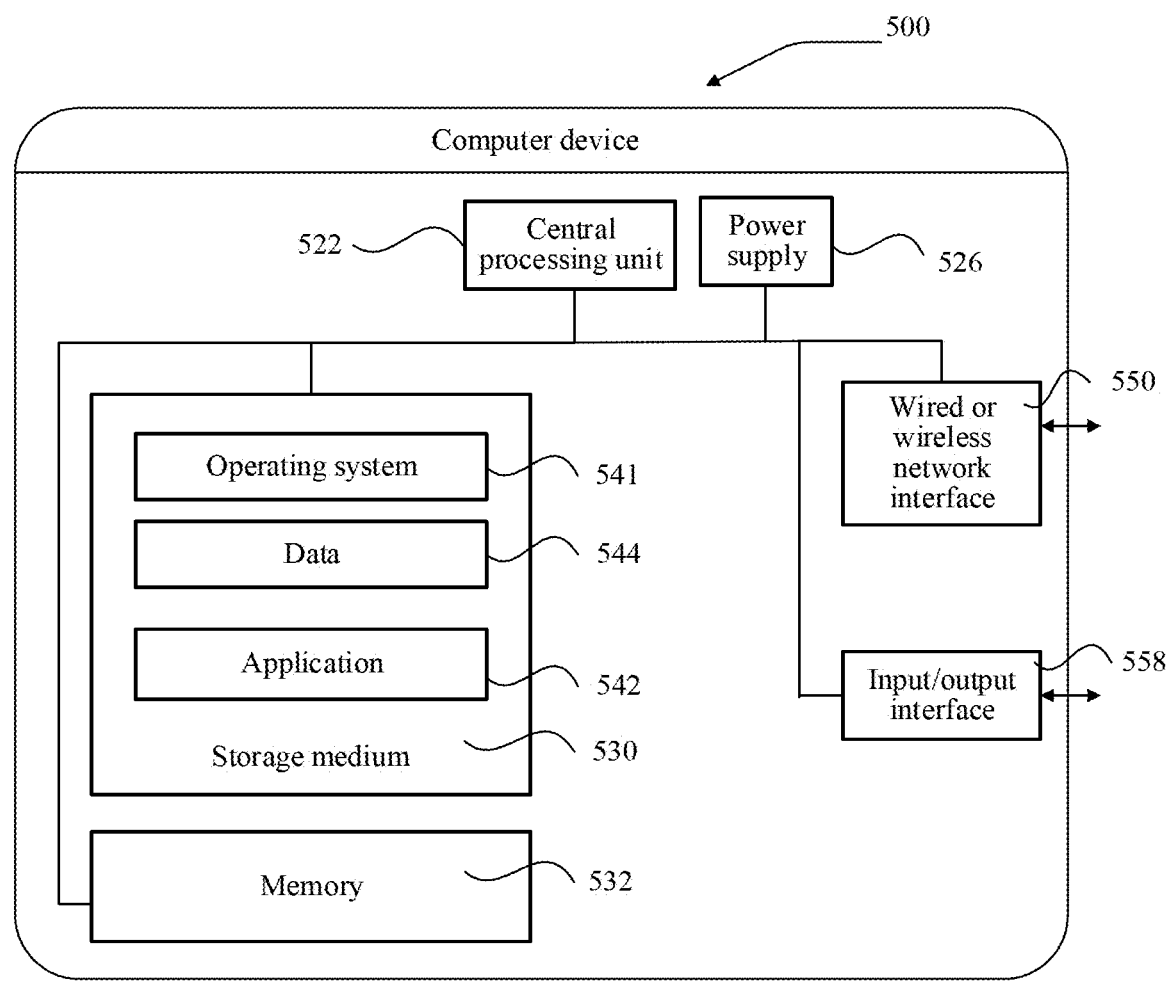
FIG. 18 is a schematic structural diagram of a computer device according to an exemplary embodiment of the present disclosure.

FIG. 18 is a schematic structural diagram of a computer device according to an exemplary embodiment of the present disclosure. As can be appreciated, configurations of the computer device 500 other than those described herein are also possible without departing from the scope of the present disclosure. The computer device 500 may include circuitry such as one or more central processing units (CPU) 522 (for example, one or more processors) and a memory 532, and one or more storage media 530 (for example, one or more mass storage devices) that store applications 542 or data 544. The memory 532 and the storage medium 530 may be transient or persistent storages. The program stored in the storage medium 530 may include one or more modules (not shown in the figure), and each module may include a series of instructions and operations for the computer device. Furthermore, the CPUs 522 may communicate with the storage media 530, and perform, on the computer device 500, the series of instruction and operations in the storage medium 530.

The computer device 500 may further include one or more power supplies 526, one or more wired or wireless network interfaces 550, one or more input/output interfaces 558, and/or one or more operating systems 541, for example, Windows Server™, Mac OS X™, Unix™, Linux™, or FreeBSD™.

Steps performed by the computer device in the foregoing exemplary embodiments may be based on the structure of the computer device shown in FIG. 18.

In an exemplary embodiment of this application, the CPU 522 is configured to perform the following steps. In a first step, a to-be-recognized medical image set is obtained. The to-be-recognized medical image set includes at least one to-be-recognized medical image. In a second step, a to-be-recognized area corresponding to each to-be-recognized medical image in the to-be-recognized medical image set is extracted. The to-be-recognized area is a part of the to-be-recognized medical image. In a third step, a recognition result of each to-be-recognized area is determined through a medical image recognition model. The medical image recognition model is obtained through training according to a medical image sample set. The medical image sample set includes at least one medical image sample, where each medical image sample carries corresponding annotation information, the annotation information being used for representing the type of the medical image sample. The recognition result is used for representing the type of the to-be-recognized medical image.

Optionally, in an exemplary embodiment of the present disclosure, the CPU 522 is further configured to perform the following steps. In a first step, a to-be-recognized original medical image set is obtained. The to-be-recognized original medical image set includes at least one to-be-recognized original medical image. In a second step, label information of each to-be-recognized original medical image in the to-be-recognized original medical image set is obtained. The label information includes information associated with the to-be-recognized original medical image. In a third step, in a case that the label information of the to-be-recognized original medical image satisfies a sample extraction condition, the to-be-recognized original medical image is determined to be the to-be-recognized medical image, until the to-be-recognized medical image set is obtained from the to-be-recognized original medical image set.

Optionally, in an exemplary embodiment of the present disclosure, the CPU 522 is further configured to perform the following steps. In a first step, a to-be-recognized original medical image set. The to-be-recognized original medical image set includes at least one to-be-recognized original medical image. In a second step, label information of each to-be-recognized original medical image in the to-be-recognized original medical image set. The label information includes information associated with the to-be-recognized original medical image. In a third step, the to-be-recognized original medical image is matched with a target medical image in a case that the label information of the to-be-recognized original medical image satisfies a sample extraction condition. The target medical image is a preset image template. In a fourth step, in a case that the to-be-recognized original medical image is successfully matched with the target medical image, the to-be-recognized original medical image is determined to be the to-be-recognized medical image, until the to-be-recognized medical image set is obtained from the to-be-recognized original medical image set.

Optionally, in an exemplary embodiment of this application, the CPU 522 is specifically configured to perform the following steps. In a first step, binarization is performed on each to-be-recognized medical image in the to-be-recognized medical image set according to a preset reflected value, to obtain a binary medical image corresponding to each to-be-recognized medical image. In a second step, each binary medical image is matched by using a target medical image, to extract a to-be-processed area corresponding to each binary medical image. The target medical image is a preset image template. In a third step, image smoothing is performed on each to-be-processed area, to generate a to-be-extracted outline corresponding to each to-be-processed area. The image smoothing includes performing at least one of an opening operation and a closing operation on each to-be-processed area. In a fourth step, the corresponding to-be-recognized area is extracted from each to-be-recognized medical image by using each to-be-extracted outline.

Optionally, in an exemplary embodiment of the present disclosure, the CPU 522 is further configured to perform the following steps. In a first step, the to-be-recognized area is scaled down in a case that the to-be-recognized area is larger than or equal to a first preset area. In a second step, the to-be-recognized area is scaled up in a case that the to-be-recognized area is larger than or equal to a first preset area.

Optionally, in an exemplary embodiment of this application, the CPU 522 is further configured to perform the following steps. In a first step, a reflected value interval corresponding to each to-be-recognized area is obtained. The maximum value of the reflected value interval is a first reflected value, and the minimum value of the reflected value interval is a second reflected value. In a second step, normalization is performed on each to-be-recognized area according to the reflected value interval, to obtain a normalized area. In determining a recognition result of each to-be-recognized area through a medical image recognition model, a recognition result corresponding to the normalized area of each to-be-recognized area is determined through the medical image recognition model. In performing normalization on each to-be-recognized area according to the reflected value interval to obtain a normalized area, the following equation is used:

$$x_{out} = \frac{x - x_{min}}{x_{max} - x_{min}},$$

Where X out $x_{our}$ represents the normalized area, x represents a pixel value of the to-be-recognized area, $x_{max}$ represents the first reflected value, and $x_{min}$ represents the second reflected value.

In an exemplary embodiment of the present disclosure, the CPU 522 is configured to perform the following steps. In a first step, a to-be-trained medical image sample set is obtained. The medical image sample set includes at least one medical image sample. Each medical image sample carries corresponding annotation information, and the annotation information is used for representing the type of the medical image sample. In a second step, a to-be-trained area corresponding to each medical image sample in the medical image sample set is extracted. The to-be-trained area is a part of the medical image sample. In a third step, a medical image recognition model is obtained through training according to the to-be-trained area corresponding to each medical image sample and the corresponding annotation information carried by each medical image sample.

Optionally, in an exemplary embodiment of the present disclosure, the CPU 522 is further configured to perform the following steps. In a first step, an original medical image set is obtained. The original medical image set includes at least one original medical image. In a second step, label information of each original medical image in the original medical image set is obtained. The label information includes information associated with the original medical image. In a third step, in a case that the label information of the original medical image satisfies a sample extraction condition, the original medical image is determined to be the medical image sample, until the to-be-trained medical image sample set is obtained from the original medical image set.

Optionally, in an exemplary embodiment of the present disclosure, the CPU 522 is further configured to perform the following steps. In a first step, an original medical image set is obtained. The original medical image set includes at least one original medical image. In a second step, label information of each original medical image in the original medical image set is obtained. The label information includes information associated with the original medical image. In a third step, the original medical image is matched with a target medical image in a case that the label information of the original medical image satisfies a sample extraction condition. The target medical image is a preset image template. In a fourth step, in a case that the original medical image is successfully matched with the target medical image, the original medical image is determined to be the medical image sample, until the to-be-trained medical image sample set is obtained from the original medical image set.

Optionally, in an exemplary embodiment of the present disclosure, the CPU 522 is specifically configured to perform the following steps. In a first step, binarization is performed on each medical image sample in the medical image sample set according to a preset reflected value, to obtain a binary medical image corresponding to each medical image sample. In a second step, each binary medical image is matched by using a target medical image, to extract a to-be-processed area corresponding to each binary medical image. The target medical image is a preset image template. In a third step, image smoothing is performed on each to-be-processed area, to generate a to-be-extracted outline corresponding to each to-be-processed area. The image smoothing includes performing at least one of an opening operation and a closing operation on each to-be-processed area. In a fourth step, a corresponding to-be-trained area is extracted from each medical image sample by using each to-be-extracted outline.

Optionally, in an exemplary embodiment of the present disclosure, the CPU 522 is further configured to perform the following steps. In a first step, the to-be-trained area is scaled down in a case that the to-be-trained area is larger than or equal to a first preset area, and in a second step, the to-be-trained area is scaled up in a case that the to-be-trained area is smaller than or equal to a second preset area.

Optionally, in an exemplary embodiment of the present disclosure, the CPU 522 is further configured to perform the following steps. In a first step, a reflected value interval corresponding to each to-be-trained area is obtained. The maximum value of the reflected value interval is a first reflected value, and the minimum value of the reflected value interval is a second reflected value. In a second step, normalization is performed on each to-be-trained area according to the reflected value interval, to obtain a normalized area.

The CPU 522 is also specifically configured to obtain a medical image recognition model through training according to the normalized area corresponding to each medical image sample and the corresponding annotation information carried by each medical image sample.

The CPU 522 is also specifically configured to obtain the normalized area using the following equation:

$$x_{out} = \frac{x - x_{min}}{x_{max} - x_{min}},$$

Where $x_{out}$ represents the normalized area, x represents a pixel value of the to-be-trained area, $x_{max}$ represents the first reflected value, and $x_{min}$ represents the second reflected value.

Optionally, in an exemplary embodiment of the present disclosure, the CPU 522 is specifically configured to perform the following steps. In a first step, the to-be-trained area corresponding to each medical image sample and the corresponding annotation information carried by each medical image sample are trained through a residual network resnet-18 structure by using an SGD algorithm, to obtain a training result. In a second step, a plurality of authentication set loss values are obtained according to the training result. In a third step, the medical image recognition model is determined according to the plurality of authentication set loss values.

Optionally, in an exemplary embodiment of the present disclosure, the CPU 522 is specifically configured to perform the following steps. In a first step, a target authentication set loss value from the plurality of authentication set loss values is obtained. The target authentication set loss value is the minimum value in the plurality of authentication set loss values. In a second step, a training result corresponding to the target authentication set loss value is determined as the medical image recognition model.

Optionally, in an exemplary embodiment of the present disclosure, the CPU 522 is further configured to perform the following steps. In a first step, a to-be-recognized medical image set is obtained. The to-be-recognized medical image set includes at least one to-be-recognized medical image. In a second step, a to-be-recognized area corresponding to each to-be-recognized medical image in the to-be-recognized medical image set is obtained. The to-be-recognized area is a part of the to-be-recognized medical image. In a third step, a recognition result of each to-be-recognized area is determined through the medical image recognition model. The recognition result is used for representing the type of the to-be-recognized medical image.

The exemplary embodiments of this application further provide a storage medium. The storage medium may be a non-transitory computer-readable storage medium. The non-transitory computer-readable storage medium stores at least one piece of program code (or computer-readable instructions), the program code (or computer-readable instructions) being loaded and executed by a processor to implement the following steps. In a first step, a to-be-recognized medical image set is obtained. The to-be-recognized medical image set includes at least one to-be-recognized medical image. In a second step, a to-be-recognized area corresponding to each to-be-recognized medical image in the to-be-recognized medical image set is extracted. The to-be-recognized area is a part of the to-be-recognized medical image. In a third step, a recognition result of each to-be-recognized area is determined through a medical image recognition model. The medical image recognition model is obtained through training according to a medical image sample set. The medical image sample set includes at least one medical image sample. Each medical image sample carries corresponding annotation information, where the annotation information is used for representing the type of the medical image sample. The recognition result is used for representing the type of the to-be-recognized medical image.

The embodiments of this application further provide a storage medium. The storage medium may be a non-transitory computer-readable storage medium. The non-transitory computer-readable storage medium stores at least one piece of program code (or computer-readable instructions), the program code (or computer-readable instructions) being loaded and executed by a processor to implement the following steps. In a first step, a to-be-trained medical image sample set is obtained. The medical image sample set includes at least one medical image sample. Each medical image sample carries corresponding annotation information, and the annotation information is used for representing the type of the medical image sample. In a second step, a to-be-trained area corresponding to each medical image sample in the medical image sample set is extracted. The to-be-trained area is a part of the medical image sample. In a third step, a medical image recognition model is obtained through training according to the to-be-trained area corresponding to each medical image sample and the corresponding annotation information carried by each medical image sample.

All or some of the foregoing exemplary embodiments may be implemented by using software, hardware (including circuitry), firmware, or any combination thereof. When software is used for implementation, implementation may be entirely or partially performed in the form of a computer program product (or as computer-readable instructions that are stored in a non-transitory computer-readable medium and executed by processing circuitry, for example).

The computer program product includes one or more computer-readable instructions. When the computer program instructions are loaded and executed on the computer, the procedures or functions according to the exemplary embodiments of the present disclosure are all or partially generated. The computer may be a general-purpose computer, a special-purpose computer, a computer network, or another programmable apparatus. The computer instructions may be stored in a non-transitory computer-readable storage medium, or transmitted from one computer-readable storage medium to another computer-readable storage medium. For example, the computer instructions may be transmitted from one website, computer, computer device, or data center to another website, computer, computer device, or data center in a wired (for example, a coaxial cable, an optical fiber, or a digital subscriber line (DSL)) or wireless (for example, infrared, radio, or microwave) manner. The non-transitory computer-readable storage medium may be any usable medium that can be stored in a computer, or a data storage device, such as a server or a data center, integrating one or more usable media. The available medium may be a magnetic medium (for example, a floppy disk, a hard disk, or a tape), an optical medium (for example, a digital versatile disc (DVD)), or a semi-conductive medium (for example, a solid state disk (SSD)). It may be understood by a person skilled in the art that, for the purpose of convenient and brief description, for a detailed working process of the foregoing system, apparatus, and unit, reference may be made to a corresponding process in the foregoing exemplary method embodiments. Therefore, no further description is provided here.

In the exemplary embodiments of the present disclosure, it is to be understood that the disclosed system, apparatus, and method may be implemented differently than described herein without departing from the scope of the present disclosure. Thus, the described exemplary apparatus embodiments are merely schematic, and the unit division described therein is merely logical function division and may be other division in actual implementation. For example, a plurality of units or components may be combined or integrated into another system, or some features may be ignored or not performed. In addition, the displayed or discussed mutual couplings or direct couplings or communication connections may be implemented by using some interfaces. The indirect couplings or communication connections between the apparatuses or units may be implemented in electric, mechanical, or other forms.

The units described as separate parts may or may not be physically separate, and parts displayed as units may or may not be physical units, may be located in one position, or may be distributed on a plurality of network units. Some or all of the units can be selected according to actual requirements to achieve the objectives of the solutions in the exemplary embodiments.

In addition, functional units in the embodiments of this application may be integrated into one processing unit, or each of the units may exist alone physically, or two or more units are integrated into one unit. The integrated unit may be implemented in the form of hardware (circuitry), or may be implemented in the form of software functional unit.

When the integrated unit is implemented in the form of a software functional unit and sold or used as an independent product, the integrated unit may be stored in a non-transitory computer-readable storage medium. Based on such an understanding, the technical solutions of the present disclosure essentially, or the part contributing to the related technology, or all or some of the technical solutions may be implemented in a form of a software product. The computer software product is stored in a storage medium and includes a plurality of instructions for instructing a computer device (which may be a personal computer, a server, a network device, or the like) to perform all or some of the steps of the methods described in the embodiments of this application. The foregoing storage medium includes any medium that can store program code, such as a USB flash drive, a removable hard disk, a read-only memory (read-only memory, ROM), a random access memory (random access memory, RAM), a magnetic disk, or an optical disc.

The foregoing exemplary embodiments are merely intended for describing the technical solutions of the present disclosure, and are not limiting. Although this application is described in detail with reference to the foregoing exemplary embodiments, a person of ordinary skill in the art is to understand that they may still make modifications to the technical solutions described in the foregoing exemplary embodiments or make equivalent replacements to some technical features thereof, as long as such modifications or replacements do not cause the essence of corresponding technical solutions to depart from the spirit and scope of the technical solutions of the exemplary embodiments of the present disclosure.

What is claimed is:

1. A medical image recognition method, applied to a computer device, the method comprising:
  obtaining a to-be-recognized original medical image set, the to-be-recognized original medical image set comprising at least one to-be-recognized original medical image;
  for each to-be-recognized original medical image of the to-be-recognized original medical image set,
    obtaining label information of the respective to-be-recognized original medical image in the to-be-recognized original medical image set, the label information comprising information associated with the respective to-be-recognized original medical image,
    determining whether the label information of the respective to-be-recognized original medical image satisfies a sample extraction condition, matching the respective to-be-recognized original medical image with a target medical image in a case that the label information of the respective to-be-recognized original medical image is determined to satisfy the sample extraction condition, the target medical image being a preset image template, and determining, in a case that the respective to-be-recognized original medical image is successfully matched with the target medical image, that the to-be-recognized original medical image is one of a to-be-recognized medical image set, the to-be-recognized medical image set comprising at least one to-be-recognized medical image;

extracting, with circuitry of the computer device, a to-be-recognized area corresponding to each to-be-recognized medical image in the to-be-recognized medical image set, the to-be-recognized area being a part of the to-be-recognized medical image; and determining, with the circuitry of the computer device, a recognition result of each to-be-recognized area through a medical image recognition model, the medical image recognition model being obtained through training according to a medical image sample set, the medical image sample set comprising at least one medical image sample, each medical image sample carrying corresponding annotation information, the annotation information being used for representing a type of the medical image sample, the recognition result being used for representing a type of the to-be-recognized medical image.

2. The method according to claim 1, wherein the extracting comprises:

performing binarization on each to-be-recognized medical image in the to-be-recognized medical image set according to a preset reflected value, to obtain a binary medical image corresponding to each to-be-recognized medical image;

matching each binary medical image by using a target medical image, to extract a to-be-processed area corresponding to each binary medical image, the target medical image being a preset image template;

performing image smoothing on each to-be-processed area, to generate a to-be-extracted outline corresponding to each to-be-processed area, the image smoothing comprising performing at least one of an opening operation and a closing operation on each to-be-processed area; and extracting a corresponding to-be-recognized area from each to-be-recognized medical image by using each to-be-extracted outline.

3. The method according to claim 1, wherein after the extracting, the method further comprises:

scaling down the to-be-recognized area in a case that the to-be-recognized area is larger than or equal to a first preset area; and scaling up the to-be-recognized area in a case that the to-be-recognized area is smaller than or equal to a second preset area.

4. The method according to claim 1, wherein after the extracting, the method further comprises:

obtaining a reflected value interval corresponding to each to-be-recognized area, the maximum value of the reflected value interval being a first reflected value, the minimum value of the reflected value interval being a second reflected value; and performing normalization on each to-be-recognized area according to the reflected value interval, to obtain a normalized area; and the determining the recognition result comprises:

determining a recognition result corresponding to the normalized area of each to-be-recognized area through the medical image recognition model; and the performing normalization on each to-be-recognized area according to the reflected value interval, to obtain a normalized area comprises:

obtaining the normalized area as:

$$x_{out} = \frac{x - x_{min}}{x_{max} - x_{min}},$$

wherein $x_{out}$ represents the normalized area, x represents a pixel value of the to-be-recognized area, $x_{max}$ represents the first reflected value, and $x_{min}$ epresents the second reflected value.

5. A non-transitory computer-readable storage medium, storing computer-readable instructions thereon that, when executed by a processor, cause the processor to perform the method according to claim 1.

6. A model training method, applied to a computer device, the method comprising:

obtaining a to-be-trained original medical image set, the to-be-trained original medical image set comprising at least one to-be-trained original medical image;

for each to-be-trained original medical image of the to-be-trained original medical image set obtaining label information of the respective to-be-trained original medical image in the to-be-trained original medical image set, the label information comprising information associated with the respective to-be-trained original medical image, determining whether the label information of the respective to-be-trained original medical image satisfies a sample extraction condition, matching the respective to-be-trained original medical image with a target medical image in a case that the label information of the respective to-be-trained original medical image is determined to satisfy the sample extraction condition, the target medical image being a preset image template, and determining, in a case that the respective to-be-trained original medical image is successfully matched with the target medical image, that the to-be-trained original medical image is one of a to-be-trained medical image set, the to-be-trained medical image sample set comprising at least one to-be-trained medical image, each to-be-trained medical image carrying corresponding annotation information, the annotation information being used for representing a type of the to-be-trained medical image;

extracting, with circuitry of the computer device, a to-be-trained area corresponding to each to-be-trained medical image in the to-be-trained medical image sample set, the to-be-trained area being a part of the to-be-trained medical image; and obtaining a medical image recognition model through training according to the to-be-trained area corresponding to each to-be-trained medical image sample and the corresponding annotation information carried by each to-be-trained medical image sample.

7. The method according to claim 6, wherein the obtaining a medical image recognition model comprises:
training the to-be-trained area corresponding to each to-be-trained medical image and the corresponding annotation information carried by each to-be-trained medical image through a residual network resnet-18 structure by using a stochastic gradient descent (SGD) algorithm, to obtain a training result;
obtaining a plurality of authentication set loss values according to the training result; and
determining the medical image recognition model according to the plurality of authentication set loss values.

8. The method according to claim 7, wherein the determining the medical image recognition model comprises:
determining a target authentication set loss value from the plurality of authentication set loss values, the target authentication set loss value being a minimum value in the plurality of authentication set loss values; and
determining a training result corresponding to the target authentication set loss value as the medical image recognition model.

9. The method according to claim 6, wherein after the obtaining the medical image recognition model, the method further comprises:
obtaining a to-be-recognized medical image set, the to-be-recognized medical image set comprising at least one to-be-recognized medical image;
extracting a to-be-recognized area corresponding to each to-be-recognized medical image in the to-be-recognized medical image set, the to-be-recognized area being a part of the to-be-recognized medical image; and
determining a recognition result of each to-be-recognized area through the medical image recognition model, the recognition result being used for representing a type of the to-be-recognized medical image.

10. A non-transitory computer-readable storage medium, storing computer-readable instructions thereon that, when executed by a processor, cause the processor to perform the method according to claim 6.

11. A computer device, comprising:
a memory and a processor configured to,
obtain a to-be-recognized original medical image set, the to-be-recognized original medical image set comprising at least one to-be-recognized original medical image;
for each to-be-recognized original medical image of the to-be-recognized original medical image set,
obtain label information of the respective to-be-recognized original medical image in the to-be-recognized original medical image set, the label information comprising information associated with the respective to-be-recognized original medical image,
determine whether the label information of the respective to-be-recognized original medical image satisfies a sample extraction condition,
match the respective to-be-recognized original medical image with a target medical image in a case that the label information of the respective to-be-recognized original medical image is determined to satisfy the sample extraction condition, the target medical image being a preset image template, and
determine, in a case that the respective to-be-recognized original medical image is successfully matched with the target medical image, that the to-be-recognized original medical image is one of a to-be-recognized medical image set, o the to-be-recognized medical image set comprising at least one to-be-recognized medical image;
extract a to-be-recognized area corresponding to each to-be-recognized medical image in the to-be-recognized medical image set, the to-be-recognized area being a part of the to-be-recognized medical image; and
determine a recognition result of each to-be-recognized area through a medical image recognition model, the medical image recognition model being obtained through training according to a medical image sample set, the medical image sample set comprising at least one medical image sample, each medical image sample carrying corresponding annotation information, the annotation information being used for representing a type of the medical image sample, the recognition result being used for representing a type of the to-be-recognized medical image.

12. The computer device according to claim 11, wherein the processor is configured to:
perform binarization on each to-be-recognized medical image in the to-be-recognized medical image set according to a preset reflected value, to obtain a binary medical image corresponding to each to-be-recognized medical image;
match each binary medical image by using a target medical image, to extract a to-be-processed area corresponding to each binary medical image, the target medical image being a preset image template;
perform image smoothing on each to-be-processed area, to generate a to-be-extracted outline corresponding to each to-be-processed area, the image smoothing comprising performing at least one of an opening operation and a closing operation on each to-be-processed area; and
extract the corresponding to-be-recognized area from each to-be-recognized medical image by using each to-be-extracted outline.

13. The computer device according to claim 11, wherein the processor is further configured to:
scale down the to-be-recognized area in a case that the to-be-recognized area is larger than or equal to a first preset area; and
scale up the to-be-recognized area in a case that the to-be-recognized area is smaller than or equal to a second preset area.

14. The computer device according to claim 11, wherein the processor is further configured to:
obtain a reflected value interval corresponding to each to-be-recognized area, the maximum value of the reflected value interval being a first reflected value, the minimum value of the reflected value interval being a second reflected value.

15. The computer device according to claim 14, wherein the processor is further configured to:
performing normalization on each to-be-recognized area according to the reflected value interval, to obtain a normalized area.

16. The computer device according to claim 15, wherein the processor is further configured to:
determine a recognition result corresponding to the normalized area of each to-be-recognized area through the medical image recognition model; and
the processor is configured to obtain the normalized area as:

$$x_{out} = \frac{x - x_{min}}{x_{max} - x_{min}},$$

wherein $x_{out}$ represents the normalized area, x represents a pixel value of the to-be-recognized area, $x_{max}$ represents the first reflected value, and $x_{min}$ represents the second reflected value.

* * * * *